United States Patent
Dueri et al.

(10) Patent No.: US 12,324,738 B2
(45) Date of Patent: *Jun. 10, 2025

(54) HYDRAULIC DELIVERY SYSTEMS WITH FLOW DIVERSION DEVICES AND ASSOCIATED METHODS

(71) Applicant: Twelve, Inc., Redwood City, CA (US)

(72) Inventors: Jean-Pierre Dueri, Los Gatos, CA (US); Gavin Kenny, Galway (IE); Jason Fox, San Mateo, CA (US); Matthew McLean, San Francisco, CA (US)

(73) Assignee: Twelve, Inc., Redwood City, CA (US)

( * ) Notice: Subject to any disclaimer, the term of this patent is extended or adjusted under 35 U.S.C. 154(b) by 242 days.

This patent is subject to a terminal disclaimer.

(21) Appl. No.: 18/053,359

(22) Filed: Nov. 7, 2022

(65) Prior Publication Data

US 2023/0083254 A1  Mar. 16, 2023

Related U.S. Application Data

(63) Continuation of application No. 16/793,904, filed on Feb. 18, 2020, now Pat. No. 11,491,007.

(Continued)

(51) Int. Cl.
*A61F 2/24* (2006.01)
*A61F 2/962* (2013.01)

(52) U.S. Cl.
CPC .......... *A61F 2/2427* (2013.01); *A61F 2/2436* (2013.01); *A61F 2/962* (2013.01)

(58) Field of Classification Search
None
See application file for complete search history.

(56) References Cited

U.S. PATENT DOCUMENTS

| 5,571,135 A | 11/1996 | Fraser et al. |
| 5,817,101 A | 10/1998 | Fiedler |

(Continued)

FOREIGN PATENT DOCUMENTS

| JP | 2022-518181 A | 9/2002 |
| JP | 2006-519053 A | 8/2006 |

(Continued)

OTHER PUBLICATIONS

International Search Report and Written Opinion of International Application No. PCT/US2020/018716, mailed Jun. 9, 2020, 12 pp.

(Continued)

*Primary Examiner* — Shaun L David

(57) ABSTRACT

A flow diversion device configured in accordance with embodiments of the present technology may include, for example, a housing including openings to channels that intersect at a junction. The flow diversion device may also include, for example, a flow control component disposed at the junction and movable to selectively form pathways for fluid communication based on a position of the flow control component. For example, when the flow control component is in a first position, a first pathway may allow fluid flow causing deployment of the prosthetic heart valve device and, when the flow control component is in a second position, a second pathway may allow fluid flow causing recapture of the prosthetic heart valve device. The flow diversion device may include a handle movable to position the flow control component in the first or second positions thereby selectively controlling fluid flow of the delivery system.

20 Claims, 15 Drawing Sheets

Related U.S. Application Data

(60) Provisional application No. 62/807,681, filed on Feb. 19, 2019.

(56) References Cited

U.S. PATENT DOCUMENTS

| | | |
|---|---|---|
| 6,113,608 A | 9/2000 | Monroe et al. |
| 6,514,261 B1 | 2/2003 | Randall et al. |
| 8,758,294 B2 | 6/2014 | Kim et al. |
| 2003/0181850 A1 | 9/2003 | Diamond et al. |
| 2008/0214979 A1 | 9/2008 | Brugger et al. |
| 2012/0022631 A1 | 1/2012 | Costello |
| 2013/0231735 A1 | 9/2013 | Deem et al. |
| 2018/0133007 A1 | 5/2018 | Prabhu |
| 2018/0296325 A1 | 10/2018 | McLean |
| 2018/0325660 A1 | 11/2018 | Mauch et al. |
| 2018/0344454 A1 | 12/2018 | Mauch et al. |

FOREIGN PATENT DOCUMENTS

| | | |
|---|---|---|
| JP | 2007-510471 A | 4/2007 |
| WO | 00/24440 A1 | 5/2000 |
| WO | 2017/165810 A1 | 9/2017 |

OTHER PUBLICATIONS

Notification of Reasons for Rejection, JP Patent Application No. 2021-540806, mailed Jan. 4, 2024.

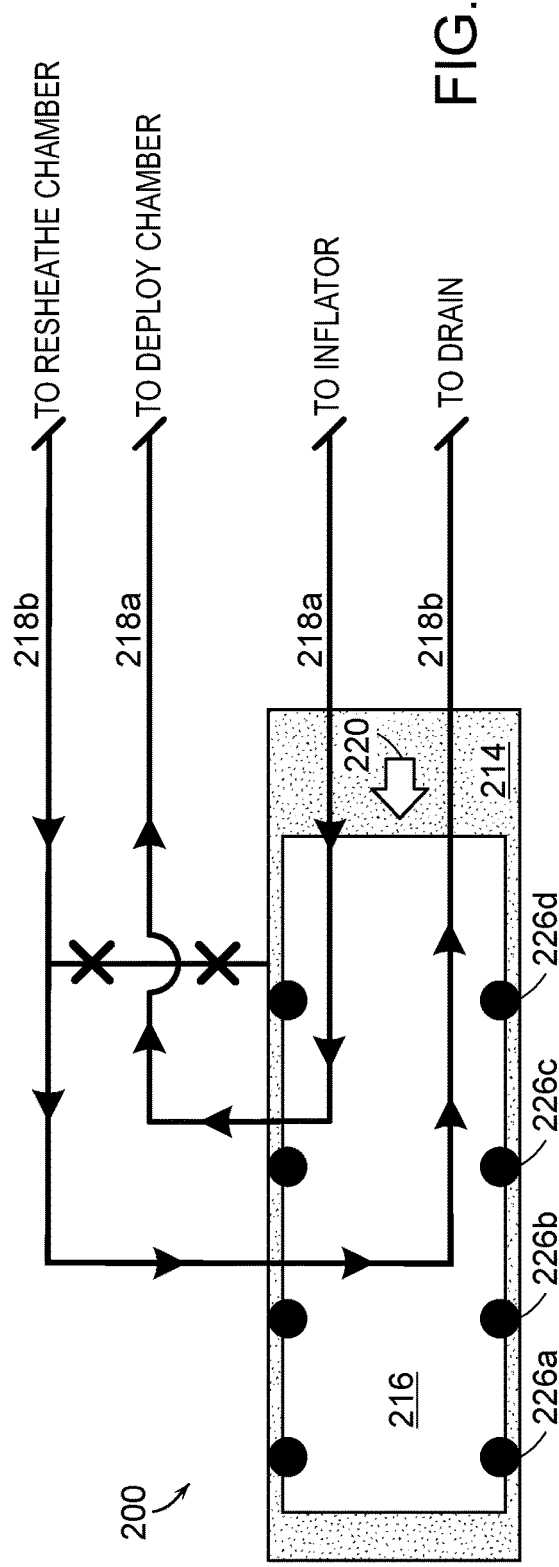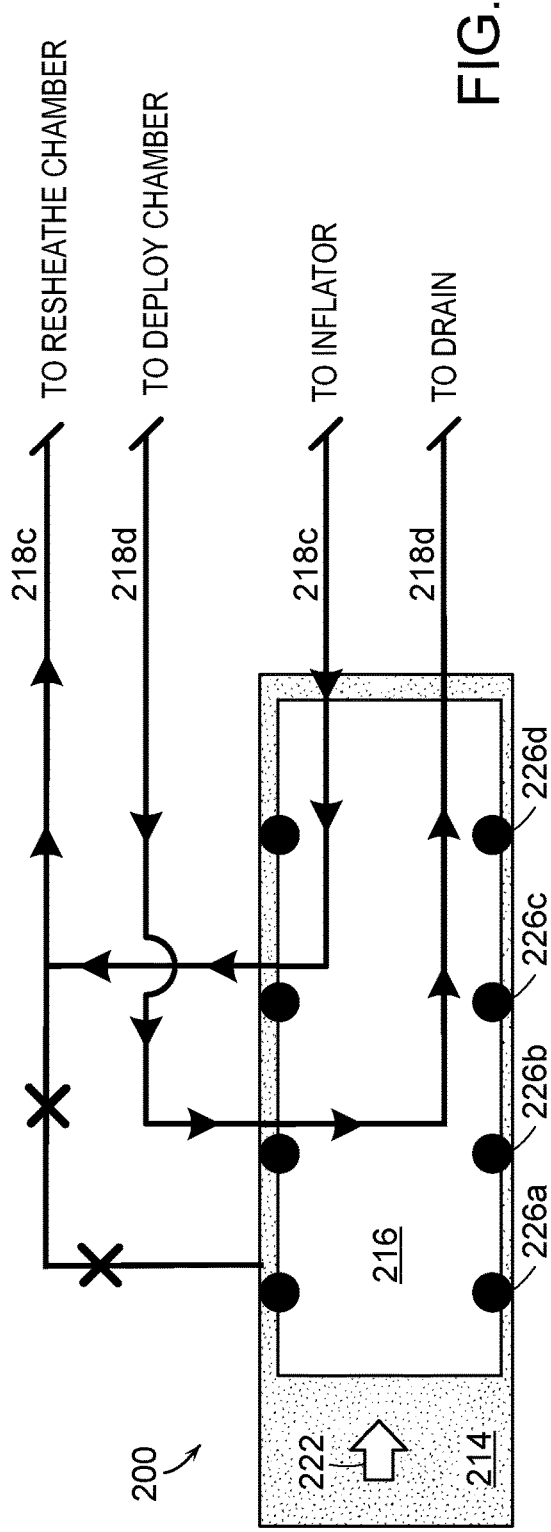

HYDRAULIC DELIVERY SYSTEMS WITH FLOW DIVERSION DEVICES AND ASSOCIATED METHODS

This application is a continuation of U.S. patent application Ser. No. 16/793,904, filed Feb. 18, 2020, which claims the benefit of U.S. Provisional Patent Application No. 62/807,681, filed Feb. 19, 2019, the entire contents of both of which are incorporated herein by reference.

TECHNICAL FIELD

The present technology relates generally to devices and systems for delivering medical devices into a patient. In particular, several embodiments of the present technology are related to hydraulic delivery systems with flow diversion devices for deploying prosthetic heart valve devices, and associated methods.

BACKGROUND

Heart valves can be affected by several conditions. For example, mitral valves can be affected by mitral valve regurgitation, mitral valve prolapse and mitral valve stenosis. Mitral valve regurgitation is abnormal leaking of blood from the left ventricle into the left atrium caused by a disorder of the heart in which the leaflets of the mitral valve fail to coapt into apposition at peak contraction pressures. The mitral valve leaflets may not coapt sufficiently because heart diseases often cause dilation of the heart muscle, which in turn enlarges the native mitral valve annulus to the extent that the leaflets do not coapt during systole. Abnormal backflow can also occur when the papillary muscles are functionally compromised due to ischemia or other conditions. More specifically, as the left ventricle contracts during systole, the affected papillary muscles do not contract sufficiently to effect proper closure of the leaflets.

Mitral valve prolapse is a condition when the mitral leaflets bulge abnormally up into the left atrium. This can cause irregular behavior of the mitral valve and lead to mitral valve regurgitation. The leaflets may prolapse and fail to coapt because the tendons connecting the papillary muscles to the inferior side of the mitral valve leaflets (chordae tendineae) may tear or stretch. Mitral valve stenosis is a narrowing of the mitral valve orifice that impedes filling of the left ventricle in diastole.

Mitral valve regurgitation is often treated using diuretics and/or vasodilators to reduce the amount of blood flowing back into the left atrium. Surgical approaches (e.g., open and intravascular) for either the repair or replacement of the valve have also been used to treat mitral valve regurgitation. For example, typical repair techniques involve cinching or resecting portions of the dilated annulus. Cinching, for example, includes implanting annular or peri-annular rings that are generally secured to the annulus or surrounding tissue. Other repair procedures suture or clip the valve leaflets into partial apposition with one another.

Alternatively, more invasive procedures replace the entire valve itself by implanting mechanical valves or biological tissue into the heart in place of the native mitral valve. These invasive procedures conventionally require large open thoracotomies and are thus very painful, have significant morbidity, and require long recovery periods. Moreover, with many repair and replacement procedures, the durability of the devices or improper sizing of annuloplasty rings or replacement valves may cause additional problems for the patient. Repair procedures also require a highly skilled cardiac surgeon because poorly or inaccurately placed sutures may affect the success of procedures.

Less invasive approaches to aortic valve replacement have been implemented recently. Examples of pre-assembled, percutaneous prosthetic valves include, e.g., the CoreValve Revalving® System from Medtronic/Corevalve Inc. (Irvine, CA, USA) and the Edwards-Sapien® Valve from Edwards Lifesciences (Irvine, CA, USA). Both valve systems include an expandable frame and a tri-leaflet bioprosthetic valve attached to the expandable frame. The aortic valve is substantially symmetric, circular, and has a muscular annulus. The expandable frames in aortic applications have a symmetric, circular shape at the aortic valve annulus to match the native anatomy, but also because tri-leaflet prosthetic valves require circular symmetry for proper coaptation of the prosthetic leaflets. Thus, aortic valve anatomy lends itself to an expandable frame housing a replacement valve since the aortic valve anatomy is substantially uniform, symmetric, and fairly muscular. Other heart valve anatomies, however, are not uniform, symmetric or sufficiently muscular, and thus transvascular aortic valve replacement devices may not be well suited for other types of heart valves.

Therefore, during a mitral valve replacement procedure, it is critical yet challenging to deploy an implant in a timely manner and targeted position due to the complex anatomy of a heart. Accordingly, it is desirable for delivery systems to enable complex operations in a flexible manner to facilitate targeted delivery of an implant with minimal time and procedural steps by alleviating the physical and cognitive burdens on clinicians operating the delivery systems during replacement procedures.

SUMMARY

In some examples, the disclosure relates to a flow diversion device for controlling fluid flow in a delivery system to deploy a prosthetic heart valve device. The flow diversion device comprises a housing including a plurality of channels that intersect at a junction, and a plurality of openings of the plurality of channels in fluid communication with the junction, wherein the plurality of openings includes a first opening and a second opening. The flow diversion device further comprises a flow control component disposed at the junction and movable to selectively form a plurality of pathways including a first pathway and a second pathway for fluid communication via the plurality of channels between the plurality of openings based on a position of the flow control component, wherein when the flow control component is in a first position, the first pathway is formed to allow fluid flow through at least the first opening toward a first chamber of the delivery system to cause deployment of the prosthetic heart valve device, and wherein when the flow control component is in a second position, the second pathway is formed to allow fluid flow through at least the second opening toward a second chamber of the delivery system to cause recapture of the prosthetic heart valve device. The flow diversion device further comprises a handle operably coupled to the flow control component and movable to position the flow control component in at least either the first position and the second position to selectively allow fluid flow toward at least either the first chamber or the second chamber of the delivery system.

In some examples, the disclosure relates to a system for delivering a prosthetic heart valve device into a heart of a patient. The system comprises an elongated catheter body including a delivery control component that is hydraulically driven to deploy and recapture the prosthetic heart valve device relative to the heart of the patient, and a flow diversion device including a housing including a plurality of openings of a plurality of channels that intersect at a junction, a flow control component disposed at the junction and movable to selectively form a plurality of pathways for fluid communication between the plurality of openings via the plurality of channels based on a position of the flow control component, wherein when the flow control component is in a first position, a first pathway is formed to allow fluid flow through a first opening of the plurality of openings to deploy the prosthetic heart valve device into the heart of the patient by filling a first chamber of the system, and wherein when the flow control component is in a second position, a second pathway is formed to allow fluid flow through a second opening of the plurality of openings to recapture the prosthetic heart valve device from the heart of the patient by draining the first chamber of the system. The system further comprises a handle movable to change a position of the flow control component between the first position and the second position to select from among the plurality of pathways for fluid communication with the first chamber.

In some examples, the disclosure relates to a flow diversion device that controls fluid flow in a system configured to implant a medical device in a patient. The flow diversion device comprises a housing including a plurality of openings of a plurality of channels that intersect at a junction; a flow control component disposed at the junction and movable to form one or more pathways for fluid communication between the plurality of openings based on a position of the flow control component, wherein when the flow control component is in a first position, a first pathway is formed to allow fluid flow through a first opening of the plurality of openings toward a first chamber of the delivery control component to cause deployment of the medical device; and wherein when the flow control component is in a second position, a second pathway is formed to allow fluid flow through a second opening of the plurality of openings toward a second chamber to cause recapture of the medical device; and a handle operably coupled to the flow control component and movable to change the position of the flow control component between at least the first position and the second position to selectively form any of the plurality of pathways for fluid communication with at least the first and second chambers of the delivery control component.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. The headings provided herein are for convenience only.

FIG. 10A is a partially schematic, functional illustration of the flow diversion device of FIGS. 8A and 8B in the first configuration in accordance with embodiments of the present technology.

FIG. 10B is a partially schematic, functional illustration of the flow diversion device of FIGS. 8A and 8B in the second configuration in accordance with embodiments of the present technology.

DETAILED DESCRIPTION

Figure 1:
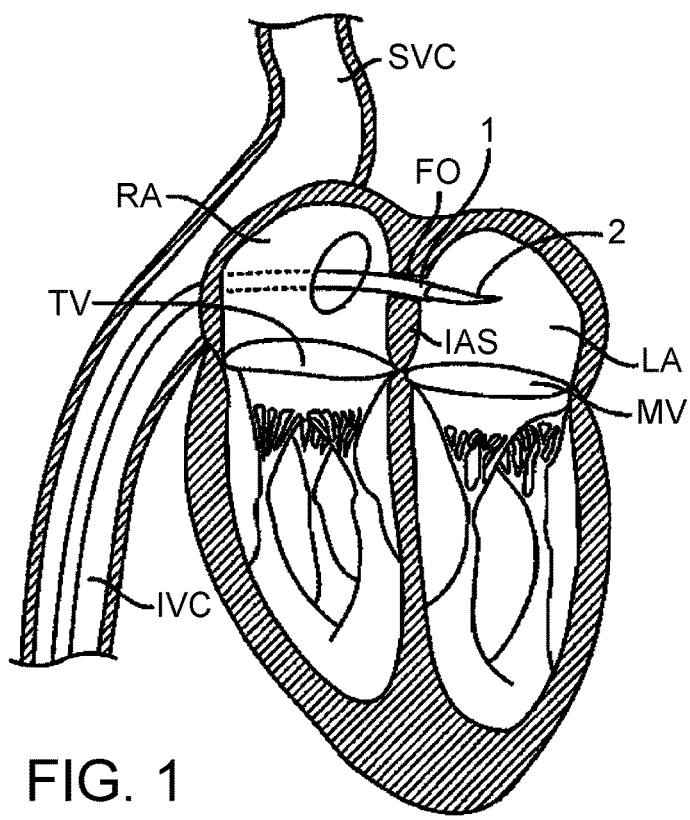
FIG. 1 is a schematic, cross-sectional illustration of the heart showing an antegrade approach to the native mitral valve from the venous vasculature in accordance with various embodiments of the present technology.

The present technology is generally directed to hydraulic delivery systems with flow diversion devices for delivering medical devices, and associated methods. Specific details of several embodiments of the present technology are described herein with reference to FIGS. 1-13. Although many of the embodiments are described with respect to devices, systems, and methods for delivering prosthetic heart valve devices to a native mitral valve, other applications and other embodiments in addition to those described herein are within the scope of the present technology. For example, at least some embodiments of the present technology may be useful for delivering prosthetics to other valves, such as the tricuspid valve or the aortic valve. It should be noted that other embodiments in addition to those disclosed herein are within the scope of the present technology. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

With regard to the terms "distal" and "proximal" within this description, unless otherwise specified, the terms can reference relative positions of portions of a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic heart valve device, the terms "proximal" and "distal" can refer to the location of portions of the device with respect to the direction of blood flow. For example, proximal can refer to an upstream position or a location where blood flows into the device (e.g., inflow region), and distal can refer to a downstream position or a location where blood flows out of the device (e.g., outflow region).

Several embodiments of the present technology are directed to delivery systems with flow diversion devices for mitral valve replacement devices that address the unique challenges of percutaneously replacing native mitral valves and are well-suited to be recaptured in a percutaneous delivery device after being partially deployed for repositioning or removing the device. Compared to replacing aortic valves, percutaneous mitral valve replacement faces unique anatomical obstacles that render percutaneous mitral valve replacement significantly more challenging than aortic valve replacement. First, unlike relatively symmetric and uniform aortic valves, the mitral valve annulus has a non-circular D-shape or kidney-like shape, with a non-planar, saddle-like geometry often lacking symmetry. The complex and highly variable anatomy of mitral valves makes it difficult to design a mitral valve prosthesis that conforms well to the native mitral annulus of specific patients. As a result, the prosthesis may not fit well with the native leaflets and/or annulus, which can leave gaps that allow backflow of blood to occur. For example, placement of a cylindrical valve prosthesis in a native mitral valve may leave gaps in commissural regions of the native valve through which perivalvular leaks may occur.

Current prosthetic valves developed for percutaneous aortic valve replacement are unsuitable for use in mitral valves. First, many of these devices require a direct, structural connection between the stent-like structure that contacts the annulus and/or leaflets and the prosthetic valve. In several devices, the stent posts which support the prosthetic valve also contact the annulus or other surrounding tissue. These types of devices directly transfer the forces exerted by the tissue and blood as the heart contracts to the valve support and the prosthetic leaflets, which in turn distorts the valve support from its desired cylindrical shape. This is a concern because most cardiac replacement devices use tri-leaflet valves, which require a substantially symmetric, cylindrical support around the prosthetic valve for proper opening and closing of the three leaflets over years of life. As a result, when these devices are subject to movement and forces from the annulus and other surrounding tissues, the prostheses may be compressed and/or distorted, causing the prosthetic leaflets to malfunction. Moreover, a diseased mitral annulus is much larger than any available prosthetic aortic valve. As the size of the valve increases, the forces on the valve leaflets increase dramatically, so simply increasing the size of an aortic prosthesis to the size of a dilated mitral valve annulus would require dramatically thicker, taller leaflets, and might not be feasible.

In addition to its irregular, complex shape, which changes size over the course of each heartbeat, the mitral valve annulus lacks a significant amount of radial support from surrounding tissue. Compared to aortic valves, which are completely surrounded by fibro-elastic tissue that provides sufficient support for anchoring a prosthetic valve, mitral valves are bound by muscular tissue on the outer wall only. The inner wall of the mitral valve anatomy is bound by a thin vessel wall separating the mitral valve annulus from the inferior portion of the aortic outflow tract. As a result, significant radial forces on the mitral annulus, such as those imparted by an expanding stent prosthesis, could lead to collapse of the inferior portion of the aortic tract. Moreover, larger prostheses exert more force and expand to larger dimensions, which exacerbates this problem for mitral valve replacement applications.

The chordae tendineae of the left ventricle may also present an obstacle in deploying a mitral valve prosthesis. Unlike aortic valves, mitral valves have a maze of cordage under the leaflets in the left ventricle that restrict the movement and position of a deployment catheter and the replacement device during implantation. As a result, deploying, positioning, and anchoring a valve replacement device on the ventricular side of the native mitral valve annulus is complicated.

During transcatheter mitral valve replacement (e.g., delivered via a transfemoral or transapical approach), it is critical to deploy the valve replacement device in a timely manner and in a correct position relative to the native annulus, leaflets, left atrium, and left ventricular outflow tract. Accordingly, it is desirable for a delivery system to enable flexible deployment and/or recapture of a valve replacement device with minimal time and procedural steps. However, conventional delivery systems include burdensome flow diversion devices such as an arrangement of multiple interconnected three-way stopcocks that must be separately adjusted to desired positions to change the direction of a delivery from deploy to recapture, or vice versa. This arrangement can be confusing and require excessive additional time such that use of conventional flow diversion devices poses a physical and cognitive burden on a clinician, and increases the risks associated with replacement procedures.

Embodiments of the present technology provide systems, methods and apparatuses to treat heart valves of the body, such as the mitral valve, that address the challenges associated with the anatomy of the mitral valve and provide for repositioning and removal of a valve replacement device. The disclosed embodiments include a flow diversion device that can perform complex operations to flexibly place a valve replacement device in a target position, in a timely manner, by reducing the physical and cognitive burdens on a clinician to operate the flow diversion device.

The disclosed embodiments overcome the aforementioned drawbacks with flow diversion devices of dual-hydraulic delivery systems that can readily and reliably deploy and/or recapture valve replacement devices. For example, a flow diversion device of the disclosed embodiments can implement a toggle mechanism that only requires a single action to switch between deploy and recapture configurations. The disclosed embodiments thus obviate the need for an arrangement of multiple interconnected three-way stopcocks, which saves the clinician time by simplifying operations for changing the delivery device from deploy to recapture configurations, or vice versa.

The disclosed systems and methods enable a percutaneous approach using a catheter delivered intravascularly through a vein or artery into the heart, or through a cannula inserted through the heart wall. For example, the systems and methods are particularly well-suited for trans-septal and transapical approaches, but can also be trans-atrial and direct aortic delivery of a prosthetic replacement valve to a target location in the heart. Additionally, the embodiments of the systems and methods as described herein can be combined with many known surgeries and procedures, such as known methods of accessing the valves of the heart (e.g., the mitral valve or triscuspid valve) with antegrade or retrograde approaches, and combinations thereof.

The disclosed flow diversion devices facilitate controlled delivery of a prosthetic heart valve device using transapical or trans-septal delivery approaches and allow resheathing of the prosthetic heart valve device after partial deployment of the device to reposition and/or remove the device. The disclosed flow diversion devices are coupled to two fluid chambers that are interchangeably filled with fluid and drained of fluid to initiate deployment and resheathing of the prosthetic device. This facilitates hydraulic control and power for both proximal and distal movement of a delivery capsule housing that provides for controlled delivery of the prosthetic heart valve device, and inhibits uncontrolled movement of the delivery system resulting from forces associated with expansion of the prosthetic heart valve device (e.g., axial jumping, self-ejection). The disclosed hydraulic delivery systems transfer forces more efficiently compared to mechanical delivery systems that experience frictional losses due to mechanical linkages between distal and proximal ends. In addition, the disclosed hydraulic delivery systems can inhibit longitudinal translation of the prosthetic heart valve device relative to the treatment site while the prosthetic heart valve device moves between the containment configuration (i.e., fully recaptured) and the deployment configuration. This allows the clinician to accurately position the sheathed prosthetic heart valve device at the desired target site for deployment, and then deploy the device at that target site without needing to compensate for any axial movement caused by deployment.

To better understand the structure and operation of valve replacement devices in accordance with the present technology, it is helpful to first understand approaches for implanting the devices. The mitral valve or other type of atrioventricular valve can be accessed through the patient's vasculature in a percutaneous manner. By percutaneous, it is meant that a location of the vasculature remote from the heart is accessed through the skin, typically using a surgical cut-down procedure or a minimally invasive procedure, such as using needle access through, for example, the Seldinger technique. The ability to percutaneously access the remote vasculature is well known and described in patent and medical literature. Depending on the point of vascular access, access to the mitral valve may be antegrade and may rely on entry into the left atrium by crossing the inter-atrial septum (e.g., a trans-septal approach). Alternatively, access to the mitral valve can be retrograde where the left ventricle is entered through the aortic valve. Access to the mitral valve may also be achieved using a cannula via a transapical approach. Depending on the approach, the interventional tools and supporting catheter(s) may be advanced to the heart intravascularly and positioned adjacent the target cardiac valve in a variety of manners, as described herein.

FIG. 1 illustrates a stage of a trans-septal approach for implanting a valve replacement device. In a trans-septal approach, access is via the inferior vena cava IVC or superior vena cava SVC, through the right atrium RA, across the inter-atrial septum IAS, and into the left atrium LA above the mitral valve MV. As shown in FIG. 1, a catheter 1 having a needle 2 moves from the inferior vena cava IVC into the right atrium RA. Once the catheter 1 reaches the anterior side of the inter-atrial septum IAS, the needle 2 advances so that it penetrates through the septum, for example at the fossa ovalis FO or the foramen ovale into the left atrium LA. At this point, a guidewire replaces the needle 2 and the catheter 1 is withdrawn.

Figure 2:
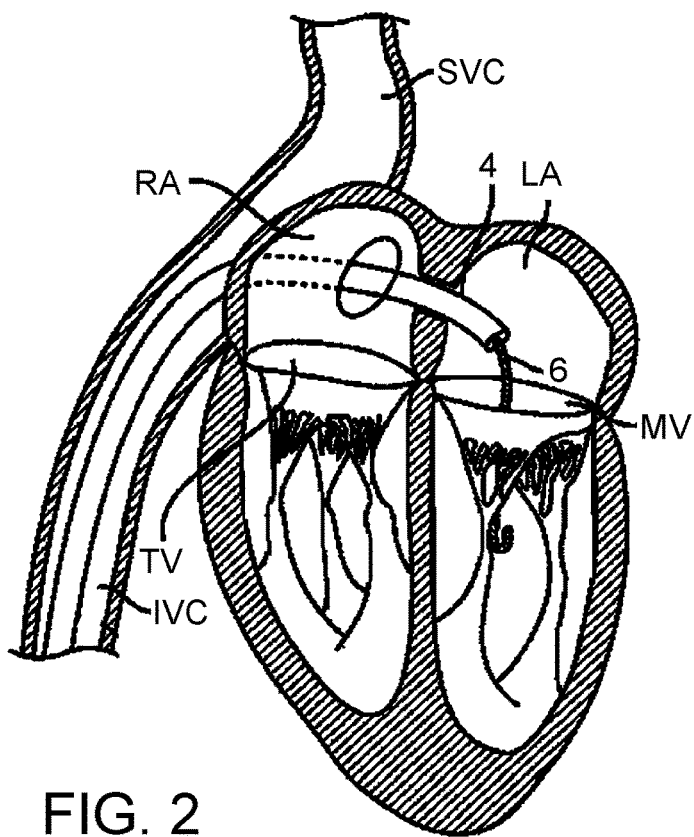
FIG. 2 is a schematic, cross-sectional illustration of the heart showing access through the inter-atrial septum (IAS) maintained by the placement of a guide catheter over a guidewire in accordance with various embodiments of the present technology.

FIG. 2 illustrates a subsequent stage of a trans-septal approach in which guidewire 6 and guide catheter 4 pass through the inter-atrial septum IAS. The guide catheter 4 provides access to the mitral valve for implanting a valve replacement device in accordance with the technology.

In an alternative antegrade approach (not shown), surgical access may be obtained through an intercostal incision, preferably without removing ribs, and a small puncture or incision may be made in the left atrial wall. A guide catheter passes through this puncture or incision directly into the left atrium, sealed by a purse string-suture.

The antegrade or trans-septal approach to the mitral valve, as described above, can be advantageous in many respects. For example, antegrade approaches will usually enable more precise and effective centering and stabilization of the guide catheter and/or prosthetic valve device. The antegrade approach may also reduce the risk of damaging the chordae tendinae or other subvalvular structures with a catheter or other interventional tool. Additionally, the antegrade approach may decrease risks associated with crossing the aortic valve as in retrograde approaches. This can be particularly relevant to patients with prosthetic aortic valves, which cannot be crossed at all or without substantial risk of damage.

Figure 3:
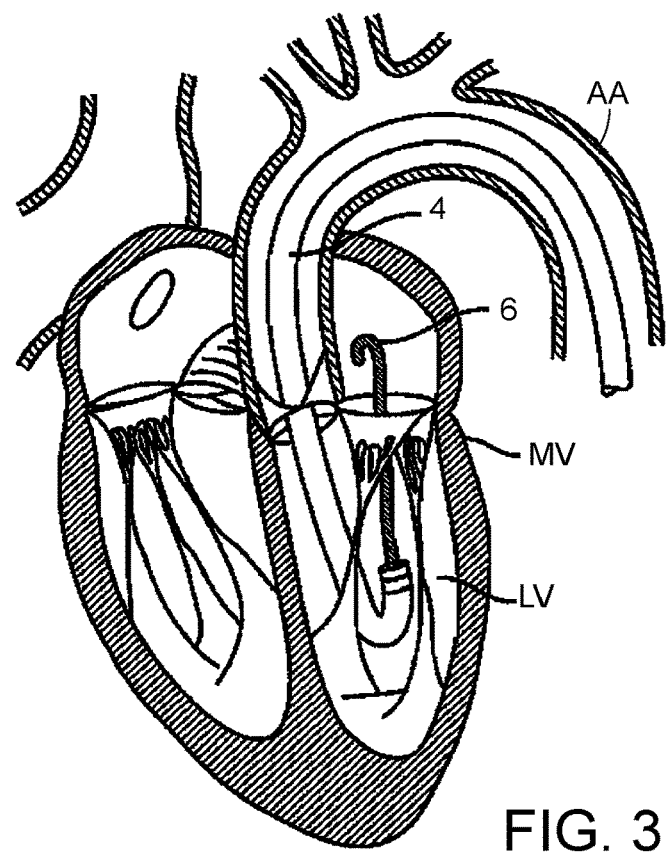
FIG. 3 is a schematic, cross-sectional illustration of the heart showing an aspect of a retrograde approach to the native mitral valve through the aortic valve and arterial vasculature in accordance with various embodiments of the present technology.
Figure 4:
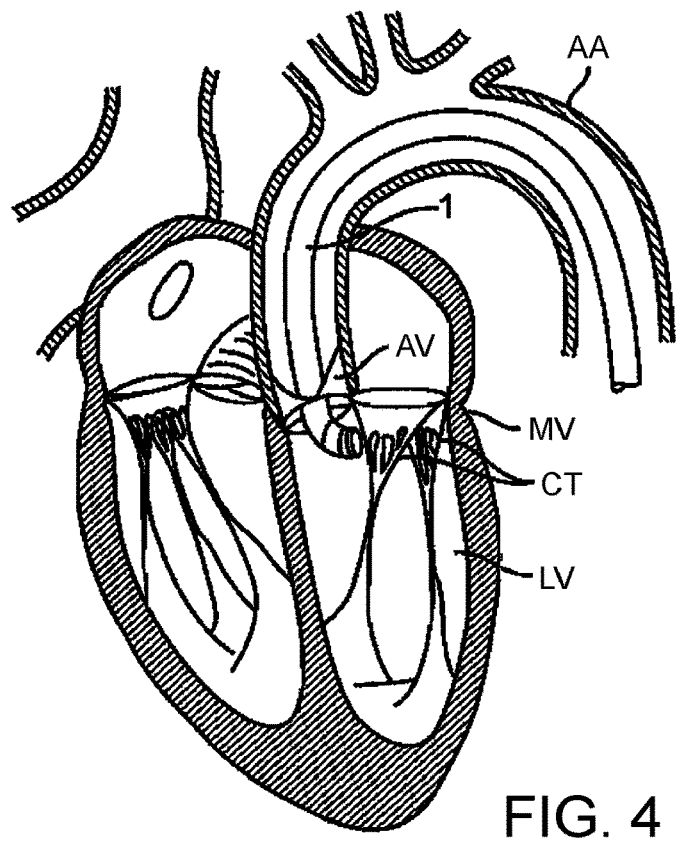
FIG. 4 is a schematic, cross-sectional illustration of the heart showing another aspect of a retrograde approach to the native mitral valve through the aortic valve and arterial vasculature in accordance with various embodiments of the present technology.

FIGS. 3 and 4 show examples of a retrograde approaches to access the mitral valve. Access to the mitral valve MV may be achieved from the aortic arch AA, across the aortic valve AV, and into the left ventricle LV below the mitral valve MV. The aortic arch AA may be accessed through a conventional femoral artery access route or through more direct approaches via the brachial artery, axillary artery, radial artery, or carotid artery. Such access may be achieved with the use of a guidewire 6. Once in place, a guide catheter 4 may be tracked over the guidewire 6. Alternatively, a surgical approach may be taken through an incision in the chest, preferably intercostally without removing ribs, and placing a guide catheter through a puncture in the aorta itself. The guide catheter 4 affords subsequent access to permit placement of the prosthetic valve device, as described in more detail herein. Retrograde approaches advantageously do not need a trans-septal puncture. Cardiologists also more commonly use retrograde approaches, and thus retrograde approaches are more familiar.

Figure 5:
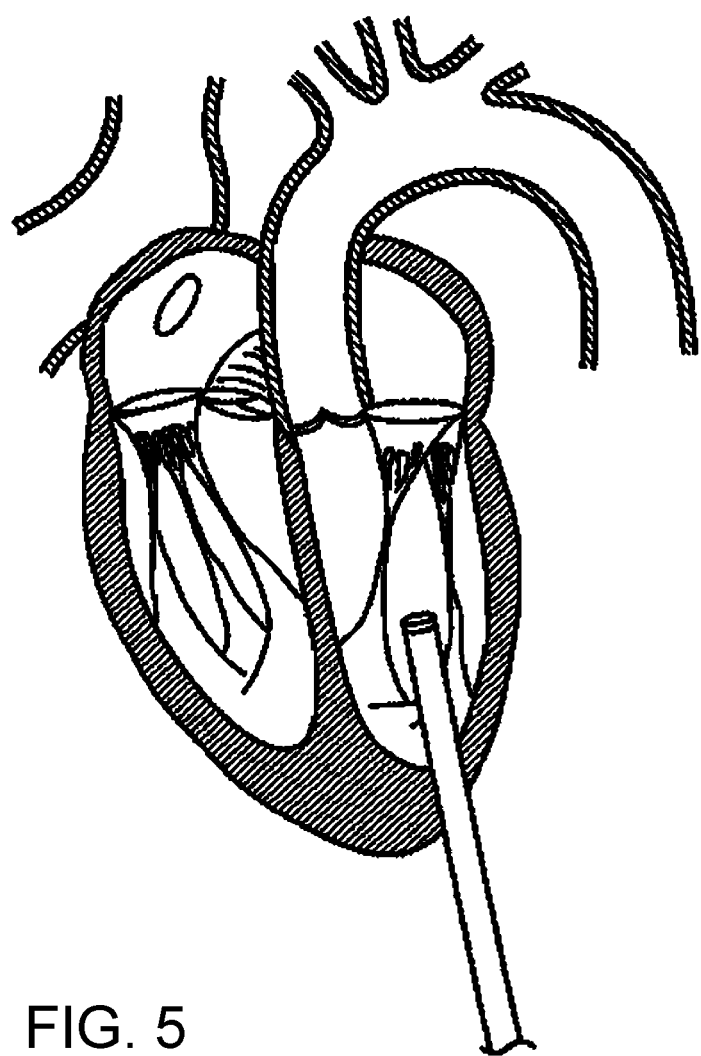
FIG. 5 is a schematic, cross-sectional illustration of the heart showing an approach to the native mitral valve using a transapical puncture in accordance with various embodiments of the present technology.

FIG. 5 shows a transapical approach via a transapical puncture. In this approach, access to the heart is via a thoracic incision, which can be a conventional open thoracotomy or sternotomy, or a smaller intercostal or sub-xyphoid incision or puncture. An access cannula is then placed through a puncture in the wall of the left ventricle at or near the apex of the heart. The catheters and prosthetic devices of the disclosure may then be introduced into the left ventricle through this access cannula. The transapical approach provides a shorter, straighter, and more direct path to the mitral or aortic valve. Further, because it does not involve intravascular access, the transapical approach does not require training in interventional cardiology to perform the catheterizations required in other percutaneous approaches.

During transcatheter heart valve replacement (e.g., delivered via transfemoral or transapical approach), it is important to deploy the prosthetic heart valve device in a controlled and efficient manner to a target position relative to the native annulus, leaflets, left atrium, and the left ventricular outflow tract (LVOT). For example, delivery systems can hydraulically control movement of a delivery capsule to reduce, limit, or substantially eliminate uncontrolled deployment (also referred to as "jumping") of the prosthetic heart valve device caused by forces associated with the expanding heart valve device. Delivery systems can also use hydraulically controlled movement to resheathe a partially or fully-expanded heart valve device to allow for repositioning of the heart valve device relative to the native anatomy and/or recapture of the device for removal from the body.

The hydraulic delivery systems described herein include flow diversion devices that facilitate changing between deployment and recapture configurations to provide bi-directional movement of delivery components. For example, the disclosed flow diversion devices do not include multiple independent stopcocks that require separate manipulation to change direction of movement of a delivery capsule. Instead, the disclosed flow diversion devices have a single actuator that can be manipulated to direct fluid in at least two different directions and, as a result, provide for the reversal of delivery capsule direction. In some embodiments, a flow diversion device has a handle that can toggle between two positions to move the delivery capsule in opposite directions, and thereby cause either deployment or recapture of a prosthetic heart valve device. As a result, the disclosed flow diversion devices simplify the process for performing complex operations to switch between deployment and recapture configurations and enhance the efficiency and ease of use of the delivery procedure.

Figure 6:
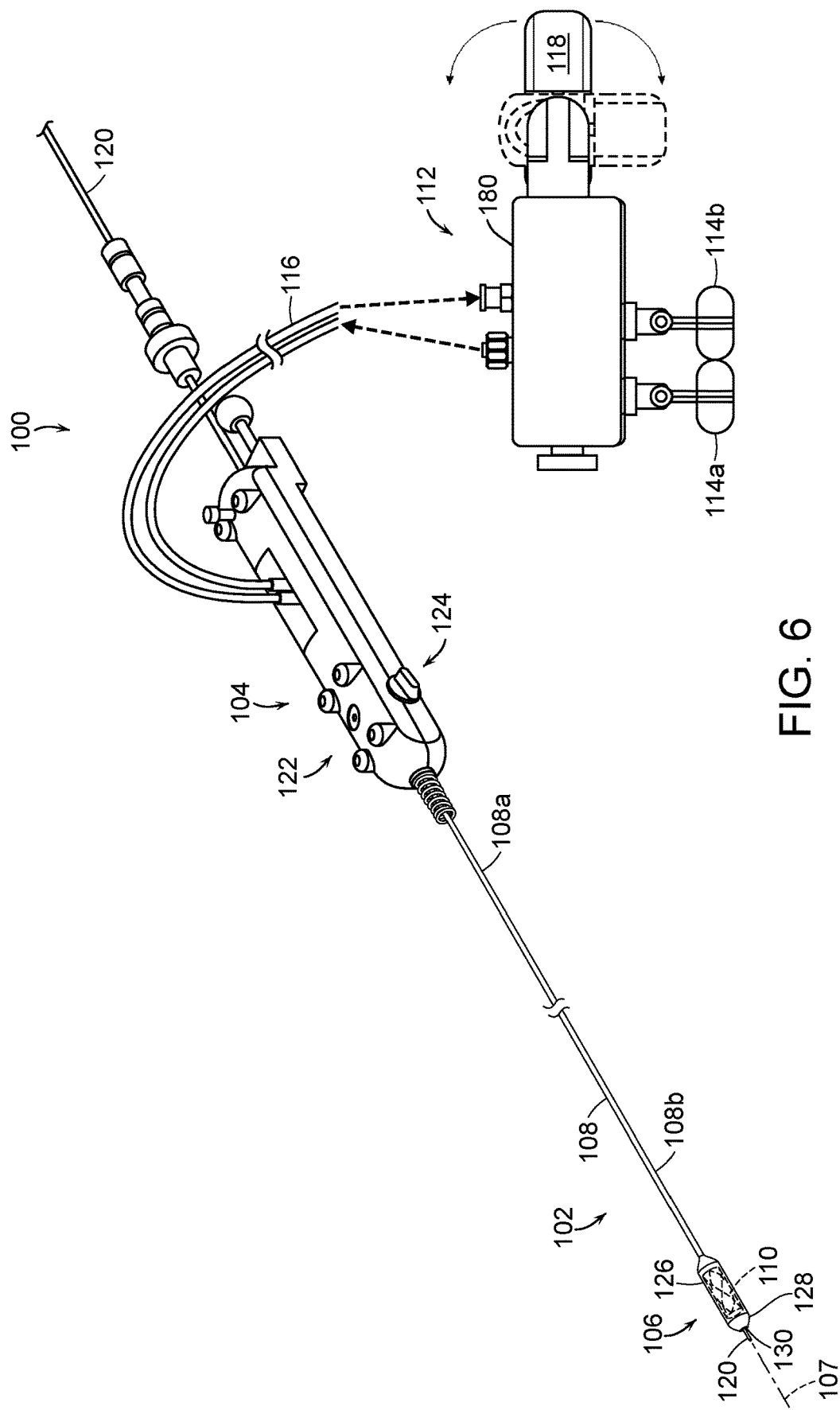
FIG. 6 is an isometric view of a delivery system for delivering a prosthetic heart valve device configured in accordance with embodiments of the present technology.

FIG. 6 is an isometric view of a hydraulic delivery system 100 ("system 100") for delivering a prosthetic heart valve device configured in accordance with embodiments of the present technology. The system 100 includes a catheter 102 with an elongated catheter body 108 and a delivery capsule 106. The catheter body 108 can include a proximal portion 108a coupled to a handheld control unit 104 and a distal portion 108b carrying the delivery capsule 106. The delivery capsule 106 can be configured to contain a prosthetic heart valve device 110 (shown schematically in broken lines). The control unit 104 can provide a steering capability (e.g., 360-degree rotation of the delivery capsule 106, 180-degree rotation of the delivery capsule 106, 3-axis steering, 2-axis steering) used to deliver the delivery capsule 106 to a target site (e.g., to a native mitral valve) and deploy the prosthetic heart valve device 110 at the target site. The catheter 102 can be configured to travel over a guidewire 120, which can be used to guide the delivery capsule 106 into the native heart valve. The system 100 also includes a flow diversion device 112 configured to supply a flowable substance (i.e., a hydraulic fluid, such as water or saline) to the catheter 102 and receive the fluid from the catheter 102, to hydraulically move the delivery capsule 106 and deploy the prosthetic heart valve device 110.

The control unit 104 can include a control assembly 122 and a steering mechanism 124. For example, the control assembly 122 can include rotational elements, such as a handle, that can be rotated to rotate the delivery capsule 106 about its longitudinal axis 107. The control assembly 122 can also include features that allow a clinician to control the hydraulic deployment mechanisms of the delivery capsule 106 and/or the flow diversion device 112. For example, the control assembly 122 can include buttons, levers, and/or other actuators that initiate unsheathing and/or resheathing of the prosthetic heart valve device 110. The steering mechanism 124 can be used to steer the catheter 102 through the anatomy by bending the distal portion 108b of the catheter body 108 about a transverse axis. In other embodiments, the control unit 104 may include additional and/or different features that facilitate delivering the prosthetic heart valve device 110 to the target site.

The delivery capsule 106 includes a housing 126 configured to carry the prosthetic heart valve device 110 in the containment configuration and, optionally, an end cap 128 that extends from an end portion of the housing 126 and encloses the prosthetic heart valve device 110 within the housing 126. The delivery capsule 106 can have an opening 130 at its distal end through which the guidewire 120 can be threaded to allow for guidewire delivery to the target site. As shown in FIG. 6, the distal portion of the delivery capsule 106 can also have an atraumatic shape (e.g., a partially spherical shape, a frusto-conical shape, blunt configuration, rounded configuration) to facilitate atraumatic delivery of the delivery capsule 106 to the target site. The housing 126, the end cap 128, and/or other portions of the delivery capsule 106 can be made of metal, polymers, plastic, composites, combinations thereof, or other materials capable of holding the prosthetic heart valve device 110.

As discussed in further detail below, the delivery capsule 106 is hydraulically driven via the control unit 104 and/or the flow diversion device 112 between a containment configuration or state for holding the prosthetic heart valve device 110 within the delivery capsule 106 and a deployment configuration or state for at least partially deploying the prosthetic heart valve device 110 from the delivery capsule 106 at the target site. The control unit and/or the flow diversion device 112 also allows for resheathing (e.g., recapture) of the prosthetic heart valve device 110 after it has been partially deployed. For example, the delivery capsule 106 can be hydraulically driven from the containment configuration towards the deployment configuration by supplying a flowable liquid to a chamber of the delivery capsule 106 while, optionally, also removing a flowable liquid from a separate chamber of the delivery capsule 106. The hydraulically controlled movement of the delivery capsule 106 is expected to reduce, limit, or substantially eliminate uncontrolled deployment of the prosthetic heart valve device 110 caused by forces associated with expansion of the prosthetic heart valve device 110, such as jumping, self-ejection, and/or other types of uncontrolled movement. For example, the delivery capsule 106 is expected to inhibit or prevent translation of the prosthetic heart valve device 110 relative to the catheter body 108 while at least a portion of the prosthetic heart valve device 110 expands. After partial deployment from the delivery capsule 106, the delivery capsule 106 can be hydraulically driven back towards the containment configuration (e.g., recapturing the device 110) by transferring fluid into one chamber of the delivery capsule 106 and, optionally, removing fluid from another chamber of the delivery capsule 106 in an opposite manner as that used for deployment. The resheathing (also referred to as recapturing herein) ability allows the clinician to reposition the prosthetic heart valve device 110, in vivo, for redeployment within the mitral valve MV or remove the prosthetic heart valve device 110 from the patient after partial deployment. After full deployment of the prosthetic heart valve device 110, the end cap 128 can be drawn through the deployed prosthetic heart valve device 110 to again close the delivery capsule 106 and draw the catheter 102 proximally through the guide catheter for removal from the patient. After removing the catheter 102, it can be sanitized and used to deliver additional prosthetic devices, or it can be discarded.

As further shown in FIG. 6, the flow diversion device 112 is fluidically coupled to the catheter 102 via one or more fluid line(s) 116. The flow diversion device 112 is also fluidically coupled to one or more reservoirs 114 (identified individually as first and second reservoirs 114a and 114b, respectively) that can contain a flowable substance (e.g., water, saline) to hydraulically drive movement of the delivery capsule 106. Each of the reservoirs 114 may include one or more fluid sources, such as an inflator device with pressurized fluid and/or a drain configured to receive drained fluid. The flow diversion device 112 and/or the fluid reservoirs 114 can also include one or more hoses, tubes, or other components (e.g., fittings, connectors, valves, pumps) through which a fluid can pass from the reservoir(s) 114 to the catheter 102, and/or through which the fluid can drain from the catheter 102 to the reservoir(s) 114. During use, the flow diversion device 112 can be manipulated to move fluid from one or more of the reservoirs 114 to the catheter 102 via the fluid line(s) 116 and/or drain fluid from the catheter 102 to one or more of the reservoirs 114 via the fluid line(s) 116.

As further shown in the embodiment illustrated in FIG. 6, the flow diversion device 112 includes an outer housing 180 that at least partially encloses a flow control mechanism for controlling the flow of fluid to and from the catheter 102 and the reservoirs 114. The flow control mechanism can include mechanical elements, such as a cylindrical member received by an elongated aperture (e.g., a bore) in the housing 180 and movable longitudinally with respect to the aperture to switch the direction of fluid flow through channels formed in part by an arrangement of sealed compartments within the housing 180. In some embodiments, the flow control mechanism includes levers, and/or other actuators to control deployment or resheathing of the prosthetic heart valve device 110. For example, the flow control mechanism can include rotational elements, such as a handle 118 that can be rotated or otherwise manipulated to cause the cylinder to move longitudinally and thereby change the direction of fluid flow along the fluid lines 116.

In some embodiments, the flow diversion device 112 and/or other portions of the system 100 are coupled to a controller (not shown) that can include, without limitation, one or more computers, central processing units, processing devices, microprocessors, digital signal processors (DSPs), and/or application-specific integrated circuits (ASICs). To store information, for example, the controller can include one or more storage elements, such as volatile memory, non-volatile memory, read-only memory (ROM), and/or random-access memory (RAM). The stored information can include, pumping programs, patient information, and/or other executable programs. The controller can further include a manual input device (e.g., a keyboard, a touch screen) and/or an automated input device (e.g., a computer, a data storage device, servers, network). In other embodiments, the controller may include different features and/or have a different arrangement for controlling the flow of fluid into and out of the reservoirs 114. In still other embodiments, one or more components or at least a portion of the flow diversion device 112 are integrated into a handle of the system 100.

Figure 7A:
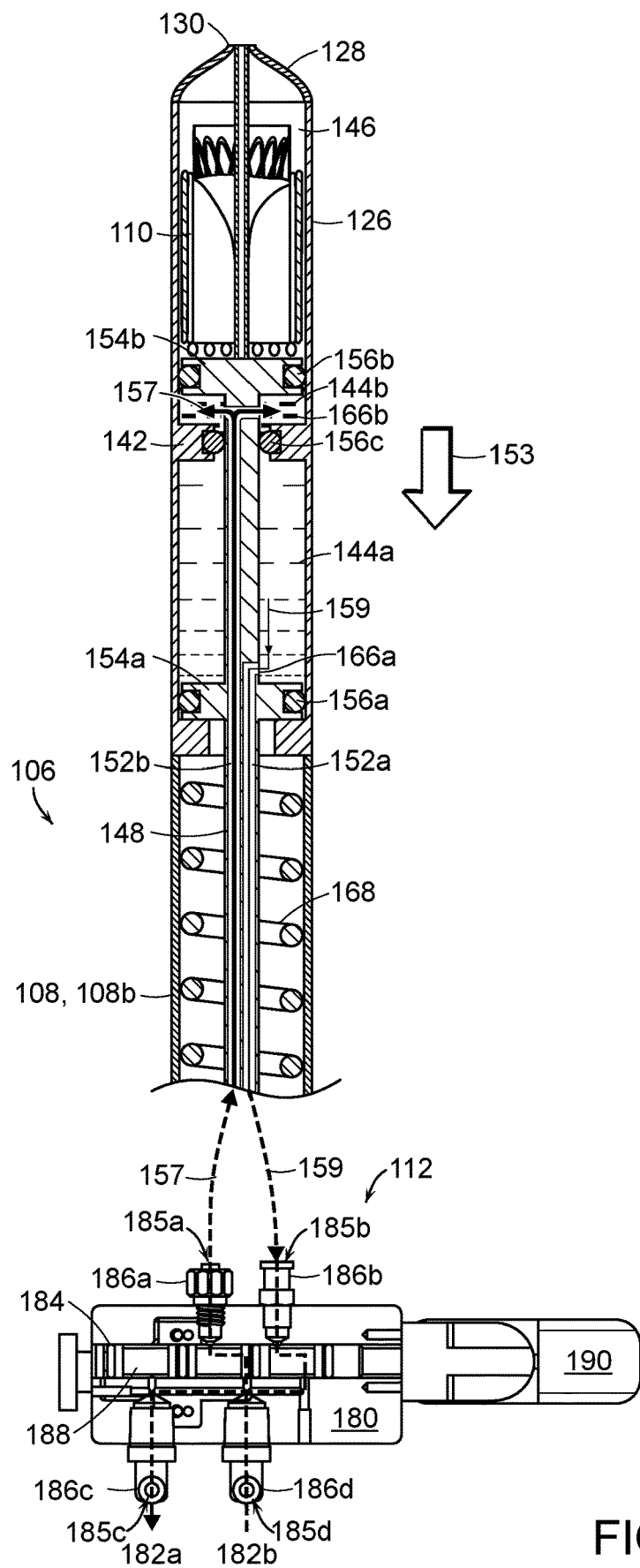
FIG. 7A is a partial cross-sectional illustration of the delivery system of FIG. 6 in a containment configuration in accordance with embodiments of the present technology.
Figure 7B:
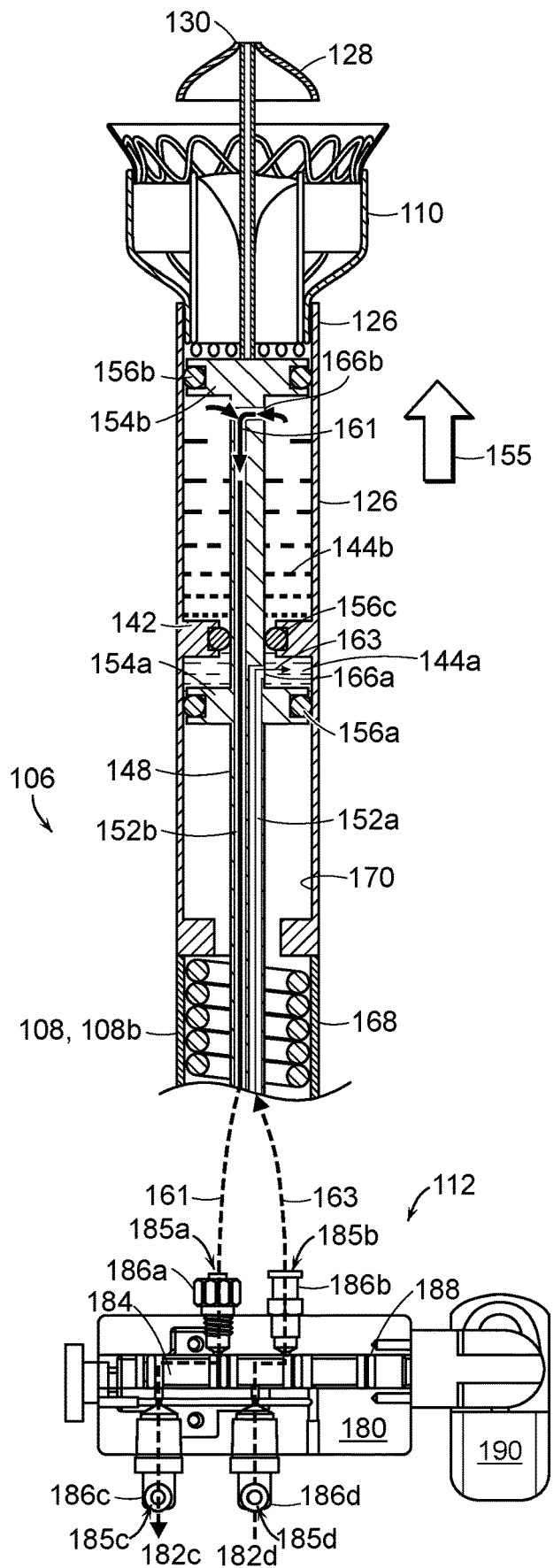
FIG. 7B is a partial cross-sectional illustration of the delivery system of FIG. 6 in a deployment configuration in accordance with embodiments of the present technology.

FIGS. 7A and 7B are partial cross-sectional views of the delivery system 100 of FIG. 6 in a containment configuration (FIG. 7A) and a deployment configuration (FIG. 7B) in accordance with embodiments of the present technology. As shown in FIGS. 7A and 7B, the distal portion 108b of the elongated catheter body 108 carries the delivery capsule 106. The delivery capsule 106 includes the housing 126 and a platform 142 that together define, at least in part, a first chamber 144a and a second chamber 144b (referred to collectively as "the chambers 144"). The first chamber 144a and the second chamber 144b are fluidically sealed from each other and from a compartment 146 in the housing 126 that is configured to contain at least a portion of the prosthetic heart valve device 110. The chambers 144 can be filled and drained to hydraulically drive the delivery capsule 106 between the containment configuration (FIG. 7A) for holding the prosthetic heart valve device 110 and the deployment configuration (FIG. 7B) for at least partially deploying the prosthetic heart valve device 110. In some embodiments, one or both of the chambers 144 are contained in the catheter body 108, the control unit 104 (FIG. 6), a different handle, and/or another portion of the system 100.

As shown in FIG. 7A, the housing 126 of the delivery capsule 106 is urged proximally (in the direction of arrow 153) towards the deployment configuration when fluid is at least partially drained from the first chamber 144a (as indicated by arrow 159) while fluid is being delivered to the second chamber 144b (as indicated by arrow 157). The proximal translation of the housing 126 allows the prosthetic heart valve device 110 to at least partially deploy from the housing 126 and expand such that it may engage surrounding tissue of a native mitral valve. As shown in FIG. 7B, the housing 126 is urged distally back towards the containment configuration to resheathe at least a portion of the prosthetic heart valve device 110 when fluid is at least partially drained from the second chamber 144b (as indicated by arrow 161) while fluid is being delivered into the first chamber 144a (as indicated by arrow 163).

The platform 142 extends at least partially between the inner wall of the housing 126 to divide the housing 126 into the first chamber 144a and the second chamber 144b. The platform 142 can be integrally formed as a part of the housing 126, such as an inwardly extending flange. Thus, the platform 142 can be made from the same material as the housing 126 (e.g., metal, polymers, plastic, composites, combinations thereof). In other embodiments, the platform 142 may be a separate component that at least partially separates the two chambers 144 from each other.

As shown in FIGS. 7A and 7B, a fluid delivery shaft 148 extends through the catheter body 108, into the housing 126 of the delivery capsule 106, and through the platform 142. At a proximal end (not shown), the shaft 148 is coupled to the flow diversion device 112 and includes one or more fluid lines 152 (identified individually as a first line 152a and a second line 152b) that can deliver and/or drain fluid to and/or from the chambers 144. The fluid lines 152 can be fluid passageways or lumens integrally formed within the shaft 148, such as channels through the shaft itself, or the fluid lines 152 may be tubes or hoses positioned within one or more hollow regions of the shaft 148. The first line 152a is in fluid communication with the first chamber 144a via a first opening 166a in the first fluid line 152a, and the second line 152b is in fluid communication with the second chamber 144b via a second opening 166b in the second fluid line 152b. In other embodiments, the first and second chambers 144a and 144b can be in fluid communication with more than one fluid line. For example, each chamber 144 may have a dedicated fluid delivery line and dedicated fluid drain line.

The shaft 148 can also include a first flange or pedestal 154a and a second flange or pedestal 154b (referred to together as "flanges 154") that extend outwardly from the shaft 148 to define the proximal and distal ends of the first and second chambers 144a and 144b, respectively. Accordingly, the first chamber 144a is defined at a distal end by a proximal-facing surface of the platform 142, at a proximal end by a distally-facing surface of the first flange 154a, and by the interior wall of the housing 126 extending therebetween. The second chamber 144b is defined at a proximal end by a distal-facing surface of the platform 142, at a distal end by a proximally-facing surface of the second flange 154b, and by the interior wall of the housing 126 extending therebetween. The compartment 146 containing the prosthetic heart valve device 110 can be defined by a distal-facing surface of the second flange 154b, the distal end of the housing 126, and the interior wall of the housing 126 extending therebetween. The shaft 148 and the flanges 154 can be integrally formed or separate components, and can be made from metal, polymers, plastic, composites, combinations thereof, and/or other suitable materials for containing fluids. The flanges 154 are fixed with respect to the shaft 148. Sealing members 156 (identified individually as first through third sealing members 156a-c, respectively), such as O-rings, can be positioned around or within the flanges 154 and/or the platform 142 to fluidically seal the chambers 144 from other portions of the delivery capsule 106. For example, the first and second sealing members 156a and 156b can be positioned in recesses of the corresponding first and second flanges 154a and 154b to fluidically seal the flanges 154 against the interior wall of the housing 126, and the third sealing member 156c can be positioned within a recess of the platform 142 to fluidically seal the platform 142 to the shaft 148. In other embodiments, the system 100 can include additional and/or differently arranged sealing members to fluidically seal the chambers 144.

The fluid lines 152 are in fluid communication with the flow diversion device 112 at a proximal portion of the system 100 (e.g., via the fluid lines 116 shown in FIG. 6). The flow diversion device 112 includes the housing 180, which encloses or defines an arrangement of interconnected channels 212 (examples of which are illustrated in further detail in FIGS. 9A and 9B) that intersect at a junction structure 184 (e.g., a tubular structure or aperture). The junction structure 184 and the channels 212 are in fluid communication with apertures or openings 203 at or accessible via the exterior of the housing 180. A plurality of fittings 186 (identified individually as first through fourth fittings 186a-d, respectively) are attached to the housing 180 and aligned with openings 185 (identified individually as first through fourth openings 185a-d, respectively) in the housing 180 to provide fluid access for fluid lines (e.g., via the fluid lines 116 shown in FIG. 6) coupling the flow diversion device to the catheter 102 (FIG. 6) and/or the reservoirs 114 (FIG. 6). The flow diversion device 112 also includes a flow control component 188 (e.g., a shaft) disposed along or within the junction structure 184 and a handle 190 operably coupled to the flow control component 188. The flow control component 188 is longitudinally and/or rotatably movable along the junction structure 184 to selectively form one or more fluid pathways 182 (identified individually in FIGS. 7A and 7B as first through fourth pathways 182a-d, respectively) along a subset of the channels 212 to provide fluid communication between the fittings 186 and the components fluidically coupled thereto (e.g., fluid lines, reservoirs, delivery capsules). Manipulating the handle 190 moves the flow control component 188 to different positions along the junction structure 184 to regulate fluid flow to and from the chambers 144 of the delivery system 100. For example, toggling the handle 190 between two different positions can move the flow control component 184 to a first position (e.g., containment or recapture configuration) and a second position (e.g., deployment configuration) to selectively allow fluid flow toward the first chamber 144a and remove fluid from the second chamber 144b, or vice versa.

As shown in FIG. 7A, when the flow control component 188 is placed in the first position (e.g., via the handle 190), the fluid control component 188 defines the first and second fluid pathways 182a and 182b for removing and delivering fluid to different chambers 144 of the delivery system 100. In the illustrated embodiment, for example, the second pathway 182b allows fluid flow from the fourth fitting 186d to the first fitting 186a toward the first chamber 144a, and the first fluid pathway 182a allows fluid to drain from the second chamber 144b. This simultaneous or concurrent fluid delivery and removal via the two pathways 182 collectively causes the delivery system 100 to move from the containment configuration to the deployment configuration and enables deployment of the prosthetic heart valve device 110.

As shown in FIG. 7B, when the flow control component 188 is positioned in a second position, the fluid control component 188 defines the third and fourth fluid pathways 182c and 182d for removing and delivering fluid to different chambers 144. In the illustrated embodiment, for example, the third pathway 182c allows fluid to drain from the second chamber 144b, while the fourth pathway 182d allows fluid flow toward the first chamber 144a. This concurrent movement of fluid to and from the chambers 144 to move the delivery system 100 from the deployed or partially deployed configuration to the containment configuration, thereby enabling recapture of the prosthetic heart valve device 110.

Therefore, movement of the fluid control component 188 between the first and second positions causes the openings 185 and the associated fittings 186 to alternatively serve as outlets and inlets depending on whether the delivery system is moving toward a deployment configuration for unsheathing the prosthetic heart valve device 110 or toward the containment configuration for resheathing the prosthetic heart valve device 110 or overall delivery system 100 removal. In the illustrated embodiment, for example, the first opening 185a and associated first fitting 186a serves as an outlet when the flow control component 188 is in the first position for device deployment and serves as an inlet when the flow control component 188 is in the second position for device recapture or system removal. Meanwhile, the second opening 185b and the second fitting 186b serves as an inlet when the flow control component 188 is in the first position and serves as an outlet when the flow control component 188 is in the second position. The third opening 185c and the associated third fitting 186c can serve as outlet regardless of whether the flow control component 188 is in the first or second position to provide a consistent fluid drainage site, and the fourth opening 185d and associated fitting 186d can serve as an inlet to supply fluid to one or both chamber 144 regardless of the position of the flow control component 188. This enables the third and fourth fittings 186c and 186d to maintain connections to a fluid retention or drainage reservoir and a fluid supply reservoir, respectively, throughout the delivery process. In other embodiments, the flow diversion device 112 can be configured such that direction of fluid through the third and fourth fittings 186c and 186d can be reversed based on positional changes of the fluid control component 188.

During use, the system 100 is arranged in the containment configuration (FIG. 7A) when the delivery capsule 106 is delivered to the target site at a native heart valve (e.g., via a transapical or trans-septal delivery approach). To fully or partially unsheathe the prosthetic heart valve device 110, the handle 190 is manipulated to move the fluid control component 188 to the first position. This allows fluid to flow along the first fluid pathway 182b, through the first fitting 186a (as indicated by arrow 157), to the second fluid line 152b, and into the second chamber 144b. As fluid is delivered to the second chamber 144b, fluid also drains through the first fluid line 152a from the first chamber 144a, toward the second fitting 186b (as indicated by arrow 159), and through the second fluid pathway 182b. In some embodiments, fluid is transferred to the second chamber 144b and from the first chamber 144a simultaneously and, optionally, in equal quantities so that the same amount of fluid transferred out of the first chamber 144a is transferred into the second chamber 144b. In some embodiments, different amounts of fluid are drained from and transferred to the chambers 144. This concurrent transfer of fluid between the chambers 144 drives the housing 126 proximally in the direction of arrow 153 to deploy the prosthetic heart valve device 110.

In the deployment configuration shown in FIG. 7B, the delivery capsule 106 axially restrains an outflow portion of the prosthetic heart valve device 110 while an inflow portion of the prosthetic heart valve device 110 is deployed from the delivery capsule 106. After at least partial deployment, the fluid chambers 144 can be pressurized and drained in an inverse manner to move the housing 126 distally (in the direction of arrow 155) back toward the containment configuration and at least partially resheathe the prosthetic heart valve device 110. For resheathing, the handle 190 is manipulated to move the flow control component 188 to the second position. This allows fluid to drain from the second chamber 144b, through the second fluid line 152b, into the fitting 186a (as indicated by arrows 161), and along the third fluid pathway 182c. As fluid exits the second chamber 144b, fluid is also delivered to the first chamber 144a. That is, fluid moves through the fourth fluid pathway 182d, through the second fitting 186b, and to the first fluid line 152a (as indicated by arrows 163). Again, the fluid can be transferred simultaneously and/or in equal proportions from the two chambers 144. This transfer of fluid into the first chamber 144a and from the second chamber 144b drives the housing 126 distally in the direction of arrow 155 to controllably resheathe the prosthetic heart valve device 110 such that at least a portion of the prosthetic heart valve device 110 is again positioned within the compartment 146. This partial or full resheathing of the prosthetic heart valve device 110 allows a clinician to reposition or remove the prosthetic heart valve device 110 after partial deployment. The hydraulic movement of the housing 126 can provide controlled deployment and resheathing of the prosthetic heart valve device 110.

As the delivery capsule 106 moves between the containment configuration and the deployment configuration, the housing 126 moves slideably with respect to the longitudinal axis of the shaft 148, while the prosthetic heart valve device 110 at least substantially maintains its longitudinal position relative to the catheter body 108. That is, the delivery capsule 106 can substantially prevent longitudinal translation of the prosthetic heart valve device 110 relative to the catheter body 108 while the prosthetic heart valve device 110 moves between the containment configuration (FIG. 7A) and the deployment configuration (FIG. 7B). This allows the clinician to position the sheathed prosthetic heart valve device 110 at the desired target site for deployment, and then deploy the device 110 at that target site without needing to compensate for any axial movement of the device 110 as it reaches full expansion (e.g., as would need to be taken into account if the device 110 was pushed distally from the housing 126).

As further shown in FIGS. 7A and 7B, the system 100 may also include a biasing device 168 that acts on the housing 126 to urge the housing 126 toward the containment configuration. The biasing device 168 compresses as the housing 126 moves to the deployment configuration (FIG. 7B) to apply more force on the housing 126 in a distal direction toward the containment configuration. In certain embodiments, the biasing device 168 acts continuously on the housing 126, urging it toward the containment configuration, and in other embodiments the biasing device 168 only acts on the housing 126 as it is compressed during deployment. In the illustrated embodiment, the biasing device 168 is positioned within the distal portion 108b of the catheter body 108, but in other embodiments the biasing device 168 can be positioned in other portions of the system 100, such as in the handle or control unit 104 (FIG. 6). The biasing device can be a spring or other feature that urges the housing 126 and/or other portion of the delivery capsule 106 toward the containment configuration. The biasing device 168 limits or substantially prevents opening of the delivery capsule 106 attributable to the forces produced by the expanding prosthetic heart valve device 110. For example, an unsheathed portion of the prosthetic heart valve device 110 can expand outwardly from the partially opened delivery capsule 106 while the biasing device 168 inhibits further opening of the delivery capsule 106.

Figure 8A:
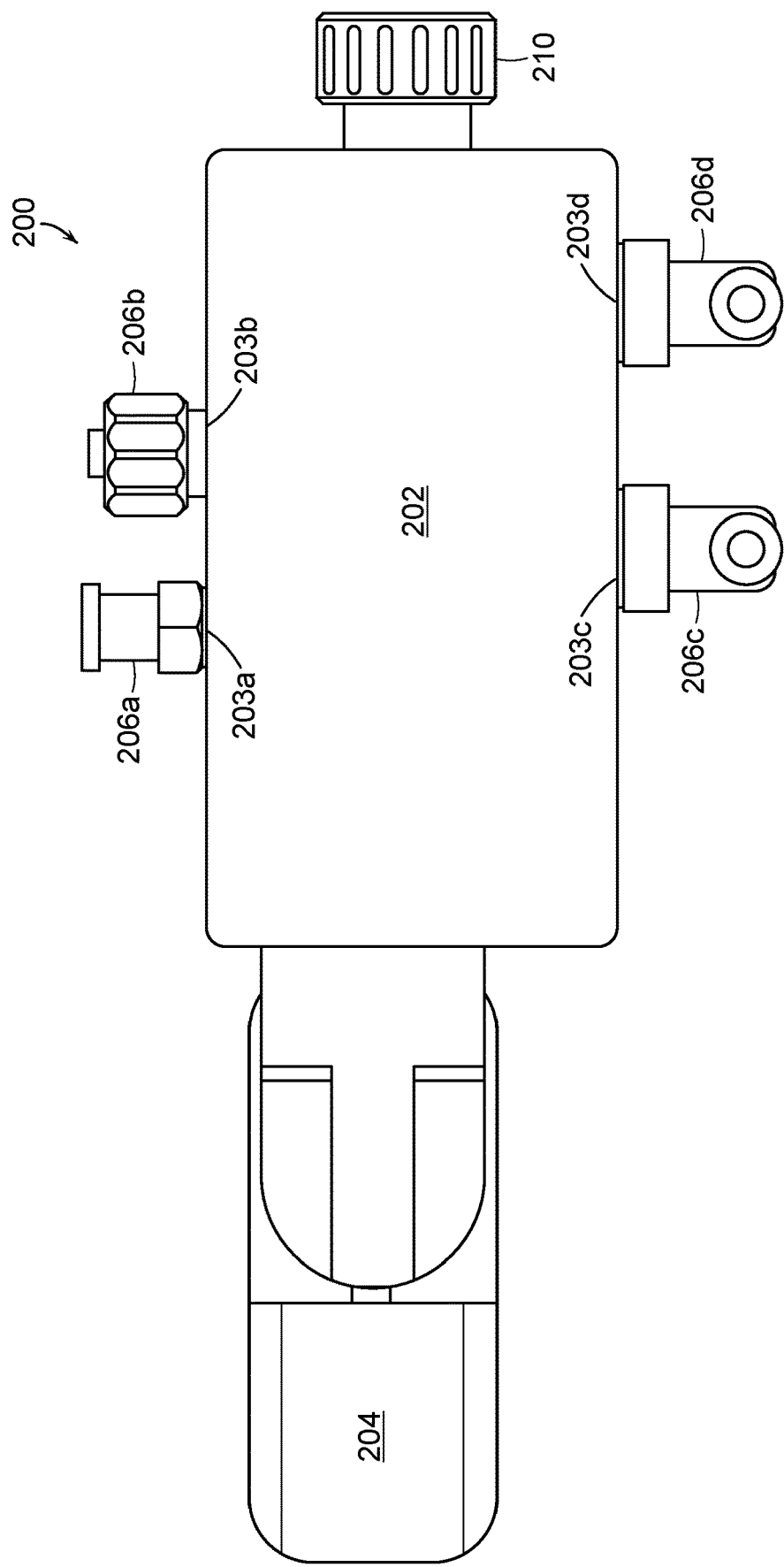
FIG. 8A is a top view of a flow diversion device configured in accordance with embodiments of the present technology.
Figure 8B:
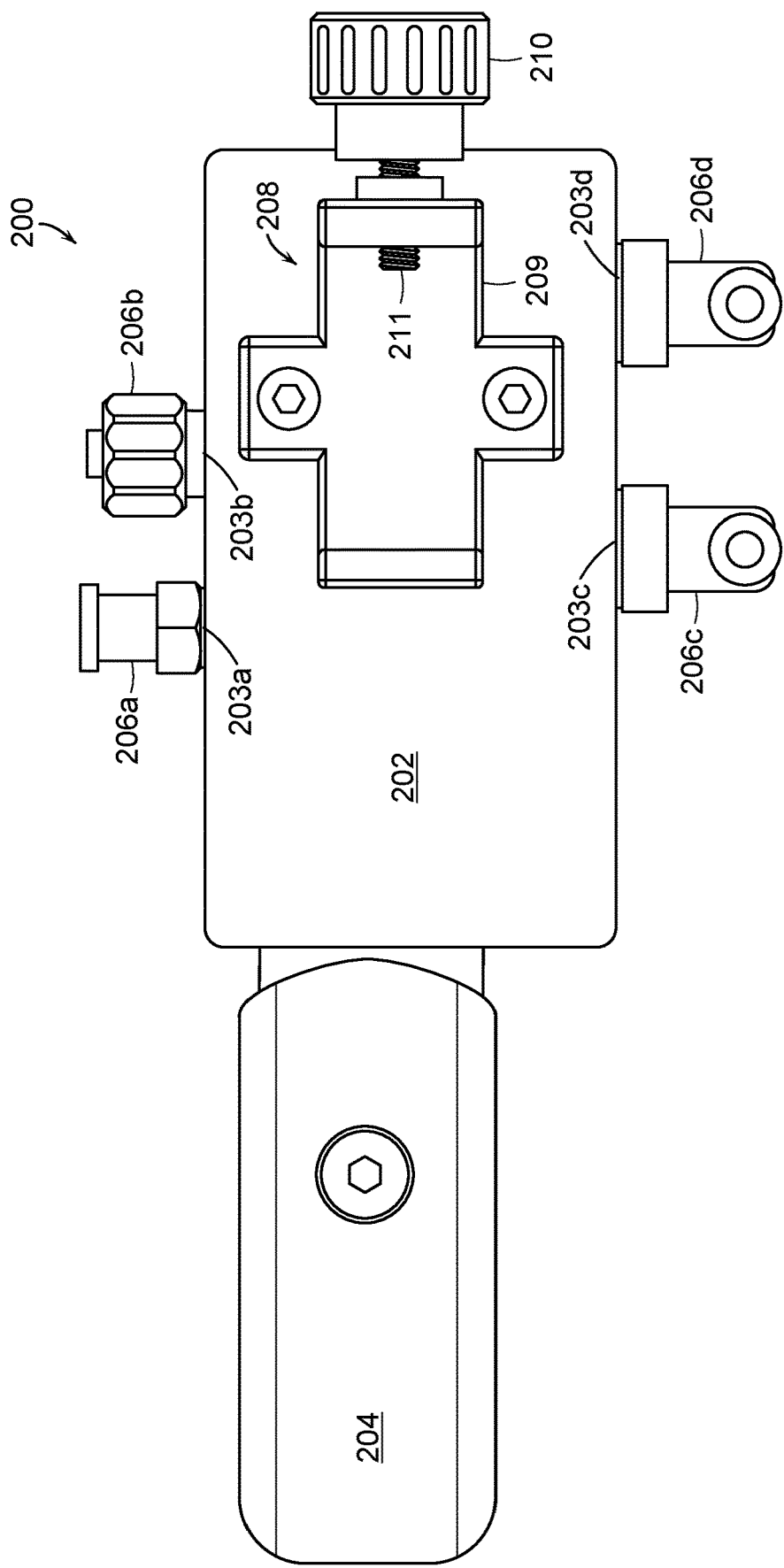
FIG. 8B is a bottom view of the flow diversion device of FIG. 8A.

FIGS. 8A and 8B illustrate top and bottom views, respectively, of a flow diversion device 200 configured to control fluid flow for deployment and recapture of an implantable device, such as a prosthetic heart valve device, in accordance with embodiments of the present technology. For example, the flow diversion device 200 can be used with the system 100 described above with respect to FIGS. 6-7B to facilitate deployment of the prosthetic heart valve device 110 at a target site (e.g., a native mitral valve, a native tricuspid valve, a native aortic valve). The flow diversion device 200 can include various features generally similar to the features of the flow diversion device 112 described above with respect to FIGS. 6-7B. For example, the flow diversion device 200 includes a housing 202 coupled to an actuator or handle 204, and the handle 204 can be toggled between at least two positions to change the path and/or the direction of fluid flow through the flow diversion device 200. In some embodiments, for example, changing the handle position enables the flow diversion device 200 to alternatingly deliver fluid to and/or remove fluid from a plurality of delivery system chambers (e.g., the chambers 144 of FIGS. 7A and 7B) fluidically coupled to the flow diversion device 200 to enable deployment and/or recapture of a prosthetic heart valve device. The flow diversion device 200 and portions thereof can be made of a variety of materials. For example, the housing 202 and/or handle 204 can be made of a rigid or semi-rigid polymer, plastic, metal, and/or other mechanically robust materials.

The flow diversion device 200 includes a plurality of apertures or openings 203 (identified individually as first through fourth openings 203a-d, respectively) in the housing 202 and a corresponding plurality of connectors or fittings 206 (identified individually as first through fourth fittings 206a-d, respectively) at least partially aligned with the openings 203. In the illustrated embodiment, the housing 202 includes four openings 203, and four fittings 206 are coupled to the housing 202 at the corresponding openings 203. In other embodiments, the flow diversion device 200 may include fewer than four or more than four openings 203 and/or fittings 206. The fittings 206 can receive or otherwise fluidically couple to one or more hoses, tubes, fluid lines, and/or other components (e.g., connectors, valves, pumps) that can concurrently deliver and/or remove fluid to/from reservoirs (e.g., the reservoirs 114 of FIG. 6), fluid chambers in a delivery catheter assembly (e.g., the chambers 144 of FIGS. 7A and 7B), and/or other components of a delivery system. For example, in the illustrated embodiment, the first and second fittings 206a and 206b can be coupled to tubes in fluid communication with respective chambers 144 of the catheter 108 (FIGS. 6-7B). The third fitting 206c can be coupled to a tube in fluid communication with an inflator device (e.g., a reservoir of an indeflator), which is filled with a pressurized fluid that can be passed to one or more chambers 144 via the flow diversion device 200. The fourth fitting 206d can be coupled to a tube in fluid communication with a drain line (e.g., reservoir), which can receive fluid drained from one or more of the chambers 144 of the catheter 108.

Figure 11:
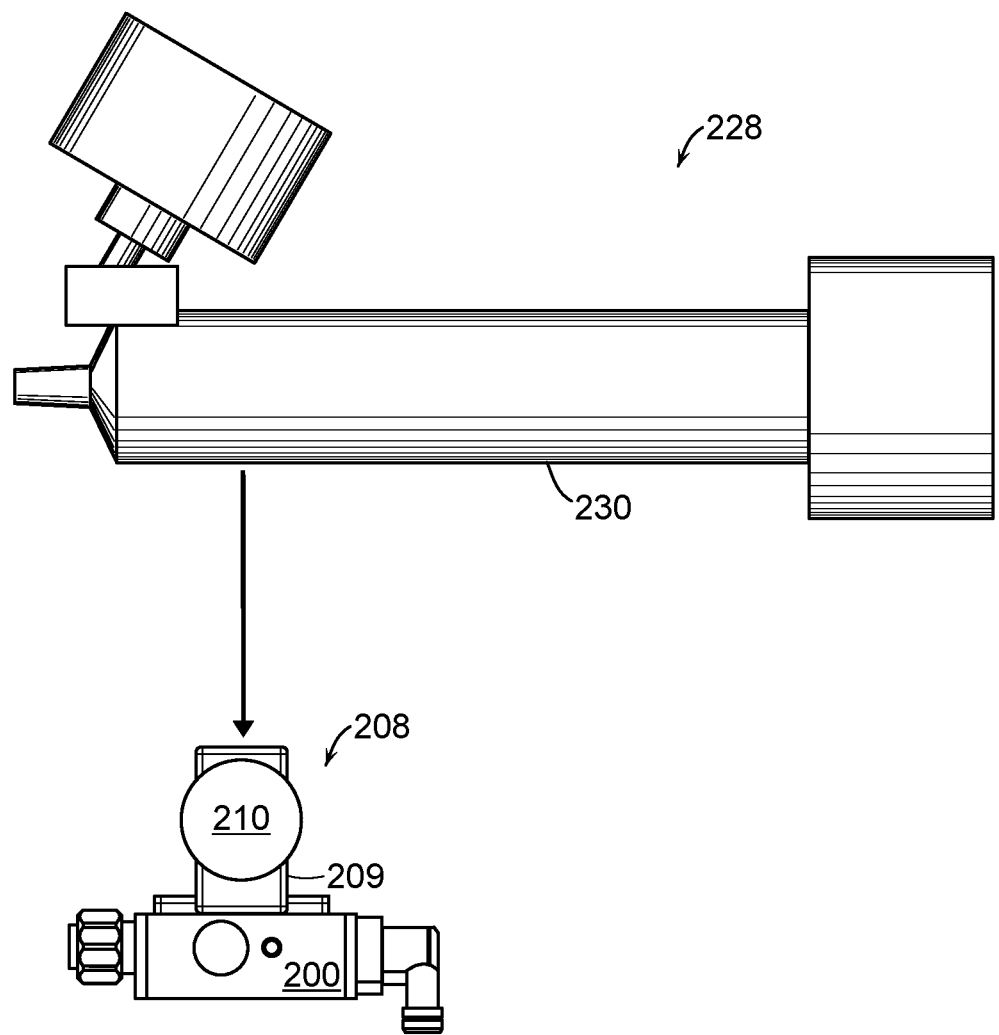
FIG. 11 is a side view of a flow diversion device connectable to an inflator device in accordance with embodiments of the present technology.

As shown in FIG. 8B, the flow diversion device 200 can include a connection device 208 that secures the flow diversion device 200 to an inflation mechanism that provides for fluid delivery to portions of the delivery catheter 108 (FIGS. 6-7B) and/or other portions of a delivery system (e.g., the system 100 of FIG. 6) The connection device 208 can include bracket 209 and a knob 210 operably coupled to a compression member 211 (e.g., a screw) that adjusts the sizing of the bracket 209 to clamp onto a portion of the delivery system. Referring to FIG. 11, for example, the connection device 208 can be positioned such that the bracket 209 extends around a portion of an inflator device 228 and the knob 210 can be rotated to adjust the sizing of the bracket 209 (e.g., adjusting the position of a screw) such that the connection device 208 applies pressure to the inflator device 228 to secure the inflator device 228 and the flow diversion device 200 together. In the embodiment illustrated in FIG. 11, the connection device 208 couples to a fluid reservoir 230 of the inflator device 228. In this and other embodiments, however, the connection device 208 can couple to other portions of the inflator device 228 or other portions of a delivery system. In other embodiments, the connection device 208 can removably secure the flow diversion device 200 to an inflator device and/or other component by an automatically adjustable spring-loaded engagement arms, a lever clamping mechanism, adhesives, and/or other suitable attachment means.

Figure 9A:
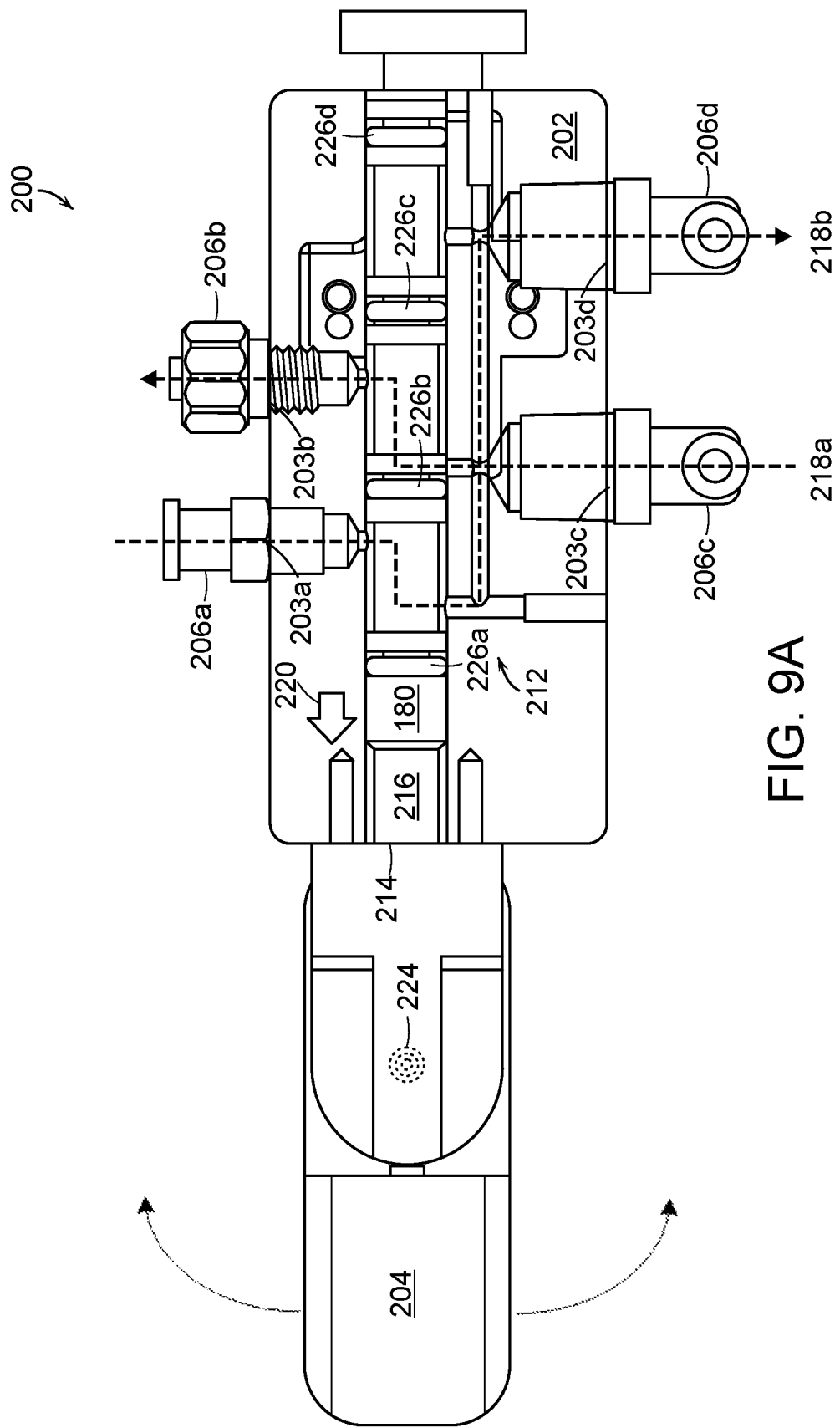
FIG. 9A is a partial cross-sectional view of the flow diversion device of FIGS. 8A and 8B in a first configuration in accordance with embodiments of the present technology.
Figure 9B:
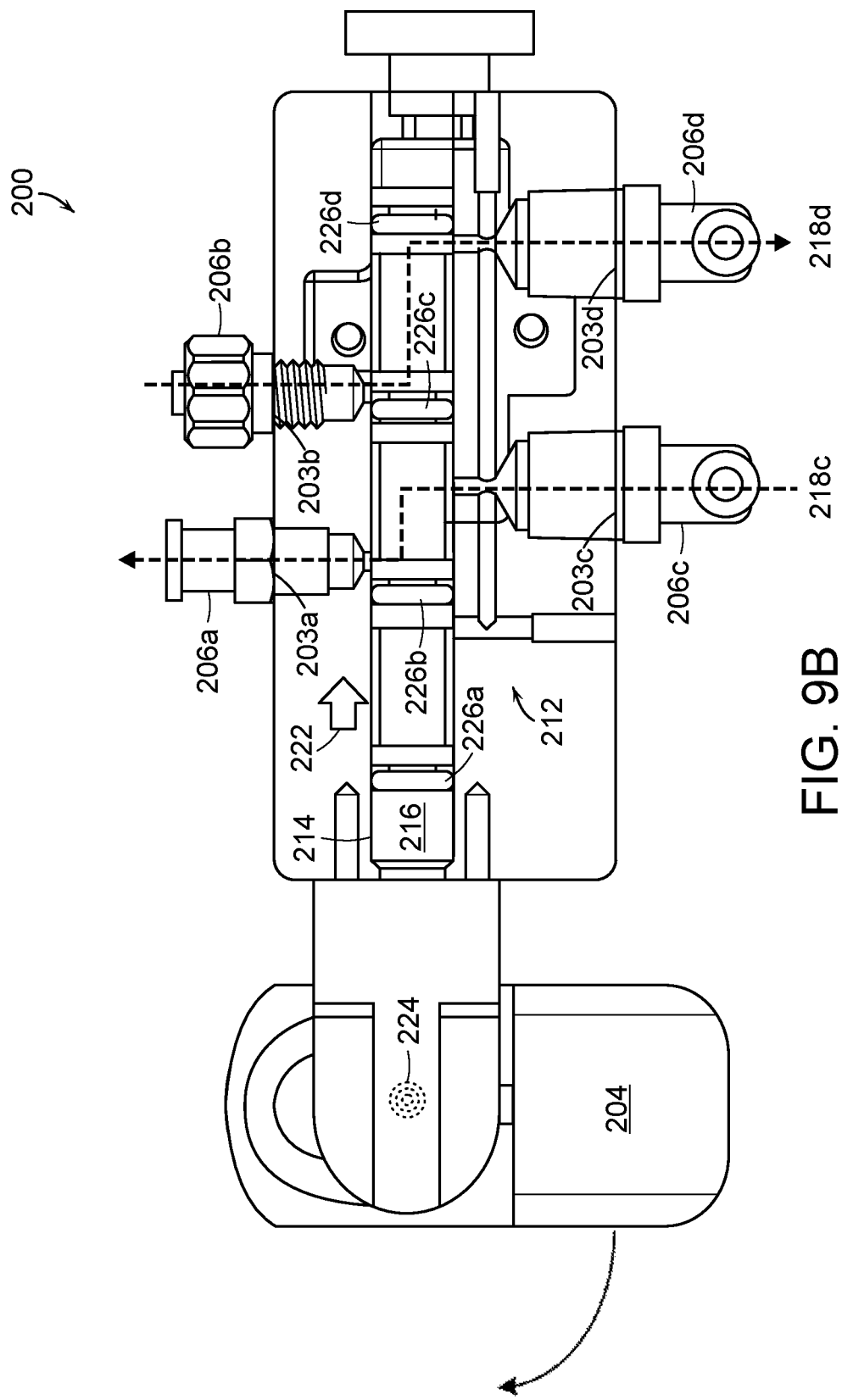
FIG. 9B is a partial cross-sectional view of the flow diversion device of FIGS. 8A and 8B in a second configuration in accordance with embodiments of the present technology.

FIGS. 9A and 9B illustrate partial cross-sectional views of the flow diversion device 200 of FIGS. 8A and 8B in two different configurations in accordance with embodiments of the present technology. Specifically, FIG. 9A illustrates a first arrangement that facilitates passing fluid to a first chamber of a hydraulic delivery system and from a second chamber of the delivery system (e.g., the chambers 144 of the delivery system 100 of FIGS. 7A and 7B). FIG. 9B illustrates a second arrangement that facilitates fluid flow in the inverse direction of the first arrangement such that fluid flows from the first chamber and to the second chamber. The flow diversion device 200 provides for the change in direction and/or path of fluid flow of the delivery system to deploy and/or recapture a prosthetic heart valve device.

As shown in FIGS. 9A and 9B, the housing 202 defines or contains a network of channels 212 that intersect at a junction structure 214, and the openings 203 and associated fittings 206 define the inlets and/or outlets for the network of channels 212. The junction structure 214 can be define by internal surfaces or walls of the housing 202 that create a hole (e.g., a borehole) and/or a separate open tube or structure extending through a portion of the housing 202. A flow control component 216 is disposed at the junction structure 214 and movable in a longitudinal and/or rotational manner within the junction structure 214 to selectively form a plurality of different fluid pathways 218 (shown in broken lines; identified individually as first through fourth pathways 218a-d, respectively) based on the orientation of the flow control component 216 to the channels 212. The flow control component 216 can be a shaft or other structure with a plurality of openings and fluid channels 212 extending therethrough such that relative movement of flow control component 216 within the junction structure 214 can align one, two, or more selected fluid channels 212 of the flow control component 216 with selected channels 212 of the housing 202 in fluid communication with the openings 203. In various embodiments, the flow control component 216 can include different or additional structures or features that allow selective activation of fluid pathways 218 through the flow diversion device 200. In some embodiments, the diameters of the flow control component 216 relative to the junction structure 214 is selected to avoid excessive fluid flow between the fluid control component 216 (e.g., a shaft) and the inner wall of the junction structure 214 (e.g., the interior surface defining a borehole) that could adversely affect fluid delivery to the delivery catheter. The fluid control component 216 and junction structure 214 can be made of a variety of materials that are mechanically robust yet reduce friction. For example, the fluid control component 216 can be made of a polycarbonate material and the junction structure 214 can be made of metal (e.g., steel), and the two features can be coated with a substance that reduces friction therebetween.

In some embodiments, the junction structure 214 includes a plurality of sealing members 226 (identified individually as first through fourth sealing members 226a-d, respectively) disposed at various locations along the flow control component 216 to form sealed compartments (i.e., between the sealing members 226a)-d. In the illustrated embodiment, the sealing members 226 are O-rings (e.g., coated rubber O-rings) disposed around the outer surface of the fluid control component 216 (e.g., a shaft) and in contact with the inner wall of the junction structure 214 (e.g., the interior surface defining a borehole). In some embodiments, at least some of the sealing members 226 can be different structures that provide sealing between portions of the flow control component 216 and the junction structure 214, yet still allow the flow control component 216 to move relative to the junction structure 214. Movement of the flow control component 216 relative to the junction structure 214 moves the compartments between the plurality of sealing members 226 into or out of alignment with the channels 212 to selectively form the pathways 218.

In FIG. 9A, the flow control component 216 is arranged in a first position to define the first and second pathways 218a-b that provide fluid communication via the network of channels 218 between the openings 203. In the illustrated embodiment, the flow control component 216 is placed in the first position by moving longitudinally along the junction structure 214 in the direction of arrow 220.

In FIG. 9B, the flow control component 216 is arranged in a second position to define the pathways third and fourth 218c-d that provide fluid communication via the network of channels 218. The flow control component 216 is placed in the second position by moving longitudinally in the direction of arrow 222 relative to the first position of the flow control component 216 shown in FIG. 9A.

As shown in FIGS. 9A and 9B, the opening 203c associated with the third fitting 206c defines an inlet of the first pathway 218a when the flow control component 216 is in the first position (FIG. 9A), and is likewise an inlet to the third pathway 218c when the fluid control component 216 is in the second position (FIG. 9B). As such, the third fitting 218c can be coupled to a fluid delivery device (e.g., an inflator) in communication with a fluid reservoir (e.g., the first reservoir 114a of FIG. 6) that can supply pressurized fluid to the flow diversion device 200 and therefrom to either a first chamber or a second chamber of a delivery system (e.g., chambers 144 of the system 100 of FIGS. 6-7B), depending on the position of the fluid control component 216. Accordingly, the third fitting 206c and associated opening 203c can define an inlet regardless of whether the delivery system is in a deployment mode or a recapture mode. In addition, the opening 203d of the fourth fitting 206d can define an outlet of the second pathway 218b when the fluid control component 216 is in the first position (FIG. 9A), and can also define an outlet of the fourth pathway 218d when the fluid delivery component 216 is in the second position (FIG. 9B). As such, the fourth fitting 206d the associated opening 203d can be coupled to a drain line or fluid receptacle that receives fluid from any of the chambers of the delivery catheter via the flow diversion device 200, regardless of the arrangement of the fluid control component 216. Accordingly, the fluid control device 200 enables the interchange between fluid delivery to and from different chambers of a delivery system without needing to move the position of the fluid delivery component or the fluid drainage component. Further, the fluid control device 200 enables this fluid interchange with a simple manipulation of a single component (i.e., the handle 204) and without undue force on the part of the clinician implementing the change between delivery and recapture of the implantable device.

Although described in terms of certain inlets or outlets of the flow diversion device 200 being configured to pass fluid in certain directions depending on the position of the flow control component 216, a person skilled in the art would understand that this is a relative arrangement of interconnections that could be achieved with a different arrangement of interconnections. For example, the description of the relative fluid flow between the flow diversion device 200 can be changed by swapping the connections between the two chambers such that, for example, the second chamber is filled and the first chamber is drained when the flow control component 200 is in the first position.

The flow control component 216 can be operably coupled to the handle 204 and/or other control structure such that manipulation of the handle 204 (e.g., toggling, turning, pushing) moves the orientation of the flow control component 216 within the junction structure 214 to the predefined first and second positions. In some embodiments, the handle 204 is operably coupled to the flow control component 216 via a pin and/or other connection structure, and rotatable about an axis 224 to position. Rotation of the handle 204 about the axis 224 to predetermined positions (e.g., first and second handle positions) can move the flow control component 216 to the first position (e.g., FIG. 9A) and the second position (e.g., FIG. 9B). In the illustrated embodiment, the first handle position (FIG. 9A) is a 90-degree rotation of the handle 204 from the neutral position, and the second handle position (FIG. 9B) is a 90-degree rotation of the handle 204 from the first handle position. In some embodiments, the handle 204 can rotate different degrees about the axis 224 to implement the different positions of the flow control component 216, the handle 204 can have additional positions that correlate to additional positions of the flow control component 216, and/or the handle 204 can be manipulated in a different or additional manner to effectuate movement onto the flow control component 216.

FIGS. 10A and 10B are partially schematic, functional illustrations of the flow diversion device 200 of FIGS. 8A-9B that further illustrate the interaction of the fluid control component 216 with the junction structure 214 to create the various fluid pathways 218 via the network of channels 212 (FIGS. 9A and 9B). FIG. 10A illustrates the flow diversion device 200 in the first or deploy configuration, and FIG. 10B illustrates the flow diversion device 200 in the second or recapture configuration.

As shown in FIG. 10A, when the flow diversion device 200 is in the deploy configuration, the flow control component 216 is in the first position. The flow control component 216 can be moved to this position by manipulating the handle 204 (FIGS. 8A-9B) to a predetermined position, which causes the flow control component 216 to move in the direction of the arrow 220. In the first position, the flow control component 216 forms the first and second pathways 218a and 218b. The first pathway 218a can place an inflator device with a fluid reservoir (e.g., the first reservoir 114a of FIG. 6) in fluid communication with a deployment chamber in a portion of a delivery catheter (e.g., one of the chambers 144 of FIGS. 7A-7B). The second pathway 218b can place a resheathe chamber of the delivery catheter (e.g., the other of the chambers 144 of FIGS. 7A-7B) with a drain or receptacle reservoir (e.g., the second reservoir 114b of FIG. 6). Thus, in the deploy configuration, the flow diversion device 200 allows for filling of the deploy chamber via the inflator device via the first pathway 218a, and removal of fluid from the resheathe chamber to the drain line via the second pathway 218b. In some embodiments, the flow diversion device 200 allows for concurrent fluid delivery to and removal from the delivery catheter, and in other embodiments these steps are performed sequentially. This fluid delivery to one chamber of the delivery system and removal from another chamber of the delivery system can initiate unsheathing of a delivery capsule from an implantable device (e.g., a prosthetic heart valve) to allow for expansion and/or deployment of the device within the body.

As shown in FIG. 10B, when the flow diversion device 200 is in the recapture configuration, the flow control component 216 is in the second position. The flow control component 216 can be moved from a neutral position or the first position (FIG. 10A) to the second position by manipulating the handle 204 (FIGS. 8A-9B) to a predetermined position, which causes the flow control component 216 to move in the direction of the arrow 222. In the second position, the flow control component 216 defines the third and fourth pathways 218c and 218d using at least some the same channels 212 (FIGS. 9A-9B) as in the deploy configuration, but redefining the connections therebetween. The third pathway 218c can place the inflator device in communication with the resheathe chamber of the delivery catheter to allow for fluid delivery to the resheathe chamber. The fourth pathway 218d can place the deploy chamber of the delivery catheter in fluid communication with a drain line to allow fluid removal from the deploy chamber. This fluid delivery to one chamber of the delivery system and fluid removal from another chamber of the delivery system, performed in an opposite manner as in the deploy configuration, can initiate resheathing or recapture of an at least partially deployed device (e.g., a prosthetic heart valve) and/or closing of a delivery capsule before removal of the delivery system from the body.

Figure 12A:
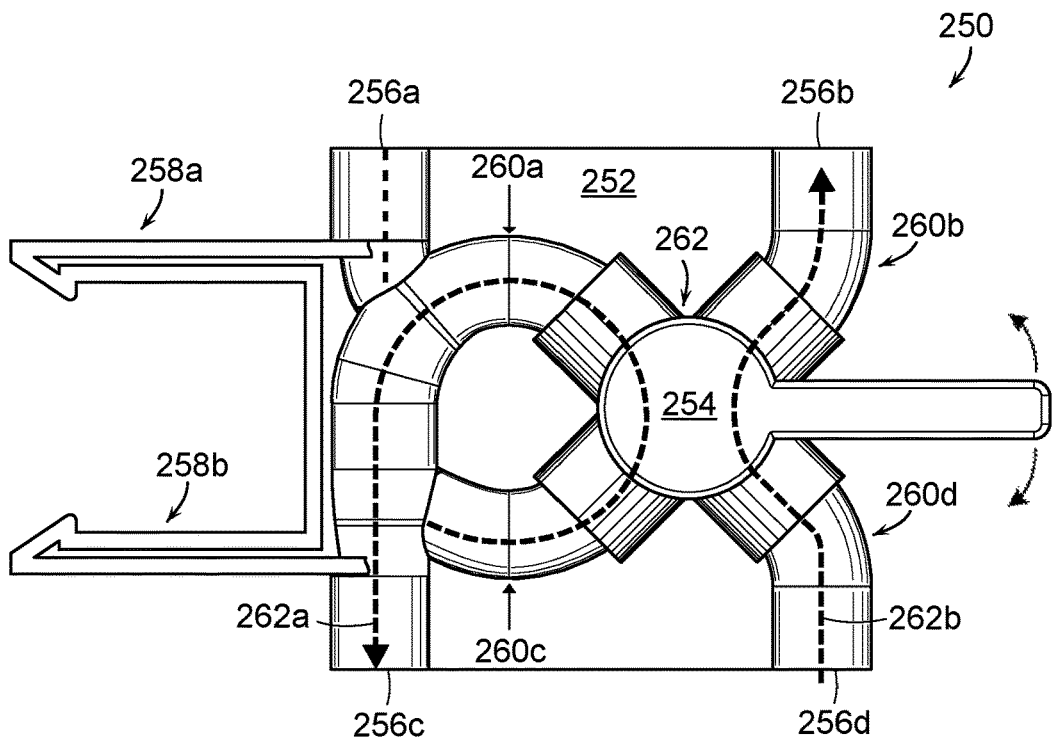
FIG. 12A is a top view of a flow diversion device in a first configuration in accordance with embodiments of the present technology.
Figure 12B:
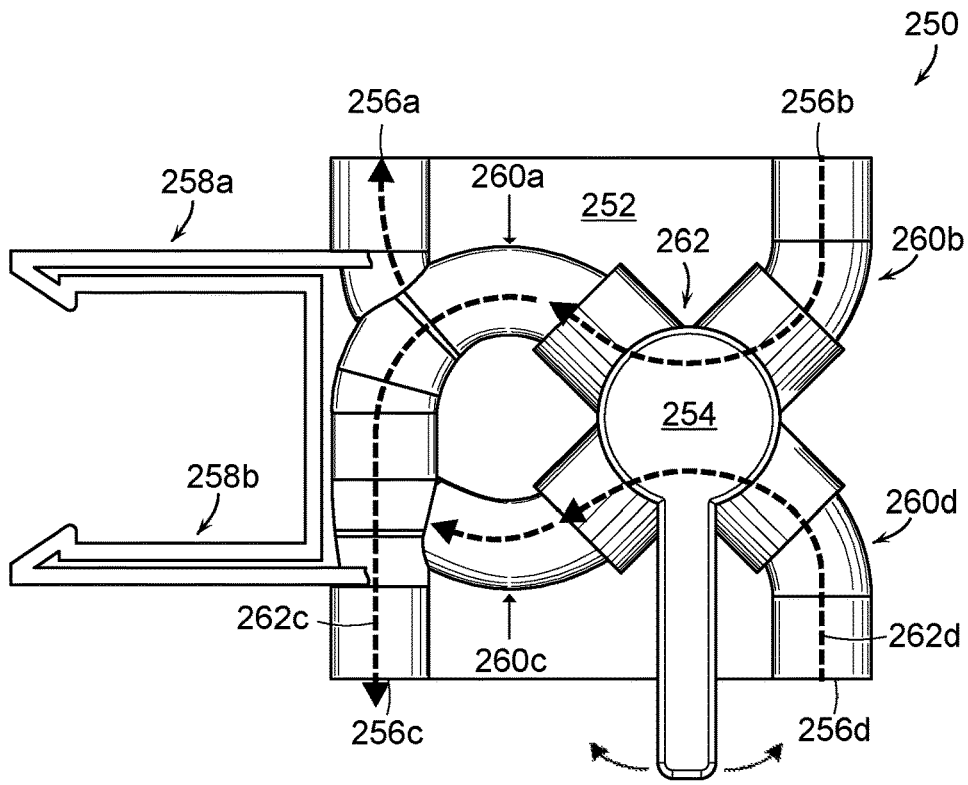
FIG. 12B is a top view of the flow diversion device of FIG. 12A in a second configuration in accordance with embodiments of the present technology.
Figure 12C:
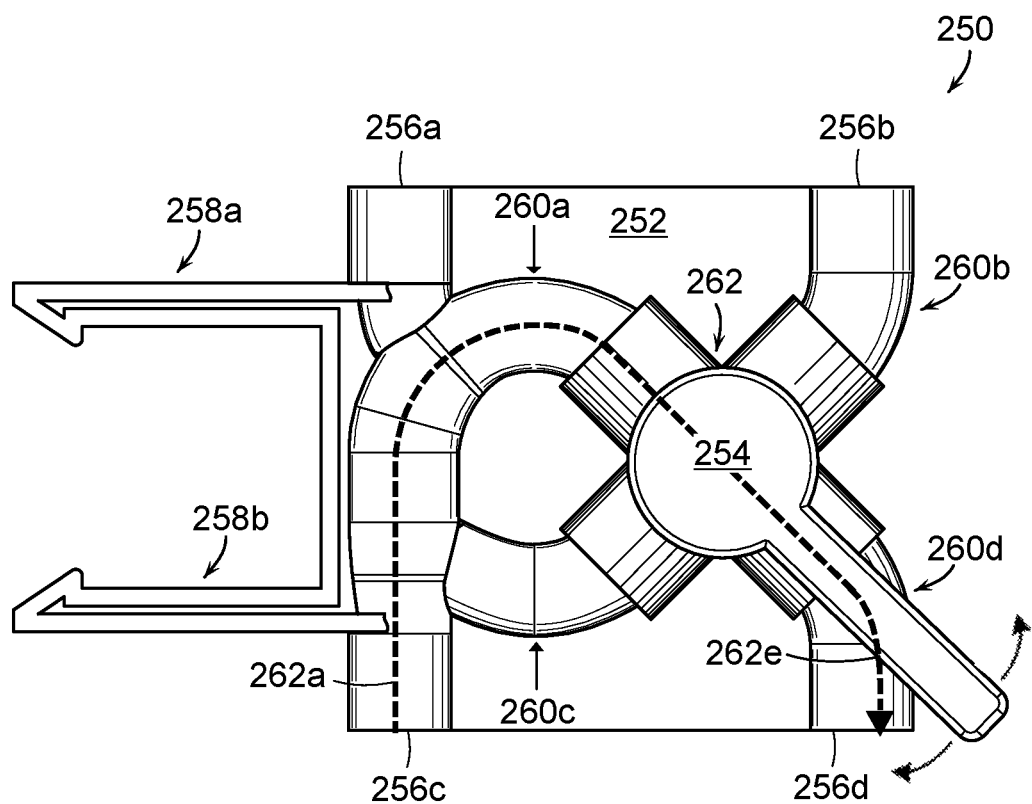
FIG. 12C is a top view of the flow diversion device of FIGS. 12A and 12B in a third configuration in accordance with embodiments of the present technology.
Figure 13:
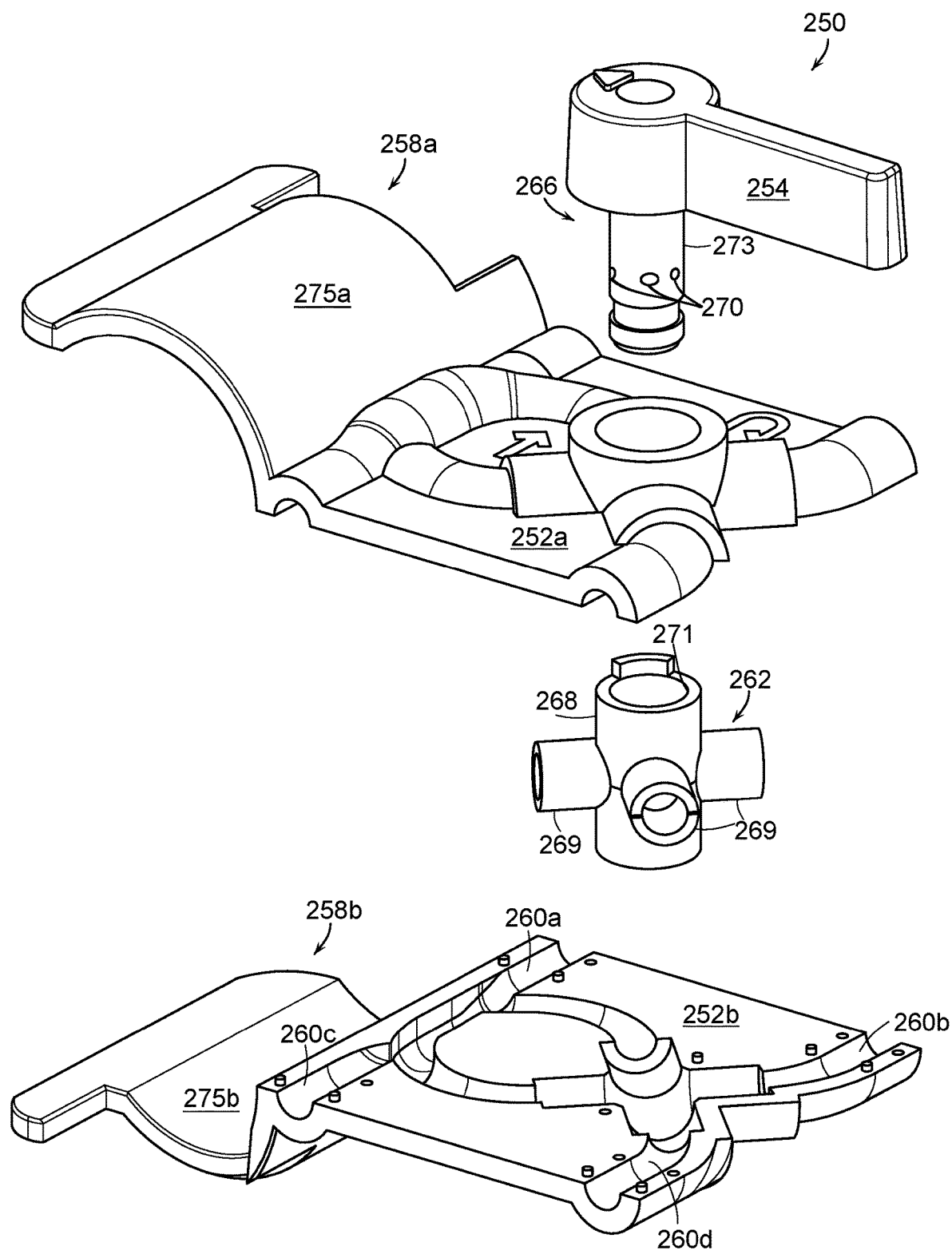
FIG. 13 is a partially exploded view of the flow diversion device of FIGS. 12A-12C.

FIGS. 12A-12C are top views of a flow diversion device 250 in various different flow arrangements in accordance with other embodiments of the present technology, and FIG. 13 is an exploded view of the flow diversion device 250 of FIGS. 12A-12C. Similar to the flow diversion device 200 of FIGS. 9A-11, the flow diversion device 250 of FIGS. 12A-13 is configured to control the pathways and direction of fluid flow in a hydraulic delivery system (e.g., the system 100 of FIG. 6) to deploy and/or recapture a prosthetic heart valve and/or other implantable device. The flow diversion device 250 includes a housing 252 coupled to a control mechanism or handle 254. The housing 252 can include a plurality of channels 260 (identified individually as first through fourth channels 260a-260d, respectively) that terminate at a plurality of openings 256 (identified individually as first through fourth openings 256a-d, respectively) accessible via the exterior of the housing 252 and intersect at a junction structure 262. The handle 254 can be rotated or otherwise moved to at least two different positions to selectively alter fluid pathways defined along the channels 260, and thereby allowing fluid delivery to and from two chambers of a delivery system, thereby enabling deployment and recapture of an implantable device from a delivery capsule of the delivery system.

The flow diversion device 250 can be made from a variety of different rigid, semi-rigid, or flexible materials. For example, the housing 252 can be made of injection molded plastic or another rigid material that is mechanically robust. The handle 254 and other components of the flow diversion device 250 can likewise be made of a polymer, metal, and/or other mechanically robust material.

In the illustrated embodiment, the housing 252 defines four openings 256 corresponding to the four channels 260 extending from the junction structure 262. In other embodiments, the housing 252 can include fewer than four or more than four openings 256. In this and other embodiments, the housing 252 can include fewer than four or more than four channels 260 intersecting the junction structure 262. Each opening 256 can receive one or more hoses, tubes, or other components (e.g., connectors, valves, pumps) for transporting a flowable substance (e.g., liquid, saline solution, water) between fluid reservoirs, drain lines, and chambers of located in a delivery capsule, along a catheter, in a handle of the catheter, and/or in other portions of a hydraulic delivery system. For example, the first and second openings 256a and 256b can receive tubes that fluidically connect the flow diversion device 250 to respective chambers of the delivery catheter. The third opening 256c can receive a tube that fluidically connects the flow diversion device 250 to a drain or reservoir configured to receive fluid removed from one or more chamber(s) of the delivery catheter. The fourth opening 256d can receive a tube that fluidically connects the flow diversion device 250 to a fluid reservoir, such as a fluid reservoir of an inflator device (e.g., the inflator device 228 of FIG. 11), which can be delivered to the chamber(s) of the delivery catheter. Accordingly, the openings 256 can define inlets and/or outlets of the network of channels 260 from/to components external to the flow diversion device 250.

As shown in the partially exploded views of FIG. 13, the flow diversion device 250 can further include a flow control component 266 disposed at least partially within the junction structure 262 and operably coupled to the handle 254. In the illustrated embodiment, the junction structure 262 includes a central tubular structure 268, a plurality of tubular arms 269 extending from radially outward from the central tubular structure 268 in alignment with corresponding plurality of channels 260, and a junction aperture 271 configured to receive the flow control component 266. The central tubular structure 268 and tubular arms 269 can be securely contained in the housing 252 of the flow diversion device 250 when joining an upper housing portion 252a and a lower housing portion 252b. In other embodiments, the junction structure 262 can be integrally formed (e.g., molded) with the housing 252 and/or otherwise secured within the housing 252. In this and other embodiments, the junction structure 262 can have different configurations, such a s a single tubular shaft without tubular arms, a tube with arms spaced in different configurations than shown, and/or other suitable junction mechanisms for supporting the flow control component 266 and interfacing with the channels 260.

The flow control component 266 includes a body portion 273, such as a shaft or other structure, that is rotatably received within the aperture 271 of the junction structure 268. The body portion 273 includes one or more diversion channels 270 (e.g., two diversion channels, three diversion channels, four diversion channels, more than four diversion channels) that traverse the body portion 273. The diameter(s) of the diversion channels 270 are such that they can facilitate suitable pressures and speeds of fluid delivery to the catheter.

During use, rotation of the handle 254 causes the flow control component 266 to rotate with respect to the junction structure 262. This rotation causes the diversion channels 270 of the flow control component 266 to align with the main channels 260 in the housing 252, and thereby selectively define a plurality of fluid pathways 264 (identified individually as first through fifth fluid pathways 264a-e, respectively; FIGS. 12A-12C). For example, rotation of the handle 262 can rotate the body portion 273 of the flow control component 266 between at least a first position (e.g., deploy configuration) and a second position (e.g., recapture configuration) such that the diversion channels 270 are selectively aligned with the main channels 260 to enable fluid flow for device delivery and recapture.

During use, the flow diversion device 250 can have two or more functional configurations for delivering fluid to and from different components of the delivery systems. In the embodiment illustrated in FIGS. 12A-13, the flow diversion device 250 has three functional configurations: a deploy configuration shown in FIG. 12A, a recapture configuration shown in FIG. 12B, and an intermediate fill configuration shown in FIG. 12C for optional refilling of an inflator device during a delivery procedure. The flow diversion device 250 may also have fourth configuration in which all the channels 260 are blocked.

Referring to FIG. 12A, when the flow diversion device 250 is in the deploy configuration, fluid can flow along a second pathway 262b from an inflator device (e.g., the inflator device 228 of FIG. 11) or other fluid reservoir, into the fourth opening 256d, through the junction structure 262 and the flow control component 266 (FIG. 13) therein, out of the second opening 256b, and into a chamber (e.g., a deploy chamber) of a delivery catheter. In some embodiments, the deploy configuration allows fluid to simultaneously or concurrently drain along the first pathway 262a, in which fluid can flow from a resheathe chamber of the delivery catheter, into the first opening 256a, through the junction structure 262 and the flow control component 266, through the third opening 256c, and into a drain line and/or reservoir.

As shown in FIG. 12B, when the flow diversion device 250 is in the recapture configuration, fluid can flow along a fourth pathway 262d from the inflator device into the fourth opening 256d, through the junction structure 262 and the flow control component 266 therein, through the first opening 256a, and into a resheathe chamber of the delivery catheter. In some embodiments, the recapture configuration also allows fluid to be removed from the deploy chamber of the delivery catheter via the third pathway 262c. In this arrangement, fluid can flow from the deploy chamber, into the second opening 256b, through the junction structure 262 and the flow control component 266 therein, through the third opening 256c, and into the drain reservoir or line. Thus, the recapture state of the flow diversion device 250 shown in FIG. 12B illustrates a counterpart to the deployment state of the flow diversion device shown in FIG. 12A, allowing fluid to move in opposite directions from respective chambers of the delivery catheter by rotating the handle 254 (and the flow control component 266 coupled thereto) from a first position shown in FIG. 12A to a second position shown in FIG. 12B.

In both the deployment and recapture configurations of the flow diversion device 250, the fourth opening 256d defines an inlet to the flow diversion device 250, whether that be for the second pathway 262b used during the deploy configuration or the fourth fluid pathway 262d used during recapture. As such, the fourth opening 256d can be coupled to an inflator device, such as a device that includes a pressurized fluid for delivery to the flow diversion device 250 and either the first chamber or the second chamber of the delivery catheter, depending on the configuration of the flow control component 250. Similarly, the third opening 256c defines an outlet of the flow diversion device 250 for each of the first and third pathways 262a and 262c when the flow diversion device 250 is in either the deploy configuration (FIG. 12A) or the recapture configuration (FIG. 12B), respectively. As such, the third opening 256c can be coupled to a reservoir, receptacle, and/or drain that can receive fluid from either the first chamber of the second chamber, depending on the configuration of the flow diversion device 250.

As shown in FIG. 12C, when the flow diversion device 250 is in an optional fill configuration, the flow diversion device 250 allows fluid to flow along the fifth pathway 262e from the third opening 256c to the fourth opening 256d to place the inflator device or reservoir in communication with a fluid reservoir (e.g., a drainage reservoir) to allow for refilling of the inflator device. In various embodiments, this intermediate configuration can be employed when initiating the delivery system (e.g., the system 100 of FIG. 6), before device deployment or recapture. For example, during initial set up, the inflator device can be filled via the fifth pathway 262e used to flush the delivery system to remove air pockets. This may deplete the fluid supply contained in the inflator device such that it is insufficient for deployment and/or recovery procedures. Accordingly, the fill configuration of FIG. 12C enables rapid refill of the inflator device or fluid reservoir without the need to detach the inflator device from the flow diversion device 250. In various embodiments, this fill configuration can also be used during the delivery procedure if additional fluid is needed for device delivery, flushing, and/or recapture.

Although described in terms of certain openings of the flow diversion device 250 configured to pass fluid in certain directions depending on the position of a flow control component, a person skilled in the art would understand that this is a relative arrangement of interconnections that could be achieved with other arrangements of interconnections. For example, the description of the relative fluid flow between the flow diversion device 250 can be changed by swapping the connections between the two chambers.

In some embodiments, the flow diversion device 250 can also include a connection assembly 258 (comprising parts 258a and 258b) that can releasably secure the flow diversion device 250 to a portion of the delivery system (e.g., the inflator device 228 of FIG. 11). The connection assembly 258 can be a bracket structure that applies resistive forces to the component held within the connection assembly 258. As shown in FIG. 13, for example, the connection assembly 258 formed by joining a first bracket surface portion 275a and a second bracket surface portion 275b on opposing sides of the housing 252. As shown, the bracket surface portions 275 can have a large surface area to enhance the grip on the inflator device. In other embodiments, the connection assembly 258 can include different attachment mechanisms for releasably secure the flow diversion device 250 to other components of the delivery system.

Although described with reference to applications that involve implanting prosthetic valve devices, the disclosed embodiments are not so limited. For example, embodiments of the disclosed flow diversion devices described above with reference to FIGS. 6-13 can be configured to cause delivery of various other medical devices in addition, or alternative, to prosthetic valve devices for replacement of the mitral valve and/or other valves in the heart of the patient. Specific elements, substructures, advantages, uses, and/or other features described herein can be suitably interchanged, substituted or otherwise configured with one another. Furthermore, suitable elements of the embodiments described can be used as stand-alone and/or self-contained devices.

From the foregoing, it will be appreciated that specific embodiments of the disclosure have been described herein for purposes of illustration, but that various modifications may be made without deviating from the scope of the disclosure. Accordingly, the disclosure is not limited except as by the appended claims.

We claim:
1. A flow diversion device for controlling fluid flow in a delivery system to deploy a prosthetic heart valve device, the flow diversion device comprising:
　a housing including:
　　a plurality of channels; and
　　a plurality of openings in fluid communication with the plurality of channels, wherein the plurality of openings includes a first opening and a second opening; and
　a flow control component movable to selectively form a plurality of pathways including a first pathway and a second pathway for fluid communication via the plu- rality of channels between the plurality of openings based on a position of the flow control component, wherein:
when the flow control component is in a first position, the first pathway is formed to allow fluid flow through at least the first opening toward a first chamber of the delivery system to cause deployment of the prosthetic heart valve device, and
when the flow control component is in a second position, the second pathway is formed to allow fluid flow through at least the second opening toward a second chamber of the delivery system to cause recapture of the prosthetic heart valve device.

2. The flow diversion device of claim 1, wherein, when the flow control component is in the first position, a third pathway is formed to drain fluid from the second chamber while the first pathway allows fluid flow toward the first chamber of the delivery system to collectively cause deployment of the prosthetic heart valve device.

3. The flow diversion device of claim 2, wherein, when the flow control component is in the second position, a fourth pathway is formed to drain fluid from the first chamber while the second pathway allows fluid flow toward the second chamber of the delivery system to collectively cause recapture of the prosthetic heart valve device.

4. The flow diversion device of claim 3, wherein the housing further comprises:
a third opening of the plurality of openings that forms an inlet of the first pathway when the flow control component is in the first position, and forms an inlet to the second pathway when the flow control component is in the second position; and
a fourth opening of the plurality of openings that forms an outlet of the first pathway when the flow control component is in the first position, and forms an outlet of the second pathway when the flow control component is in the second position.

5. The flow diversion device of claim 1 further comprising a handle operably coupled to the flow control component and movable to position the flow control component in at least either the first position and the second position to selectively allow fluid flow toward at least either the first chamber or the second chamber of the delivery system.

6. The flow diversion device of claim 1, wherein the plurality of channels intersect at a junction.

7. The flow diversion device of claim 6, wherein the flow control component comprises:
a shaft disposed in a bore of the housing and longitudinally movable to selectively form any of the plurality of pathways based on a longitudinal position of the shaft relative to the bore.

8. The flow diversion device of claim 6 further comprising a plurality of sealing members disposed at different locations of the shaft to form sealed compartments that are movable to selectively form the plurality of pathways.

9. The flow diversion device of claim 8, wherein each of the plurality of sealing members is an O-ring disposed around the shaft.

10. The flow diversion device of claim 1, wherein the flow control component comprises a shaft disposed in the junction and rotatable to selectively form any of the pathways based on an angle of rotation of the shaft.

11. The flow diversion device of claim 10, wherein the shaft comprises at least one rotatable channel that selectively forms any of the plurality of pathways based on an angle of rotation of the shaft.

12. The flow diversion device of claim 10, wherein the flow diversion device comprises a four-way stopcock with three functional positions for diverting fluid flow.

13. The flow diversion device of claim 10, wherein when the flow control component is in a third position, a third pathway forms to allow fluid flow through a third opening of the plurality of openings towards an inflator.

14. A flow diversion device that controls fluid flow in a system configured to implant a medical device in a patient, the flow diversion device comprising:
a housing including a plurality of openings of a plurality of channels, the plurality of openings including a first opening, a second opening, a third opening, and a fourth opening; and
a flow control component disposed within the housing to form a plurality of fluid pathways for fluid communication between the plurality of openings based on a position of the flow control component, wherein:
when the flow control component is in a first position, a first fluid pathway is formed to allow fluid flow out of the housing through the first opening and a second fluid pathway is formed to allow fluid flow into the housing through the second opening; and
when the flow control component is in a second position, a third fluid pathway is formed to allow fluid flow out of the housing through the second opening and a fourth fluid pathway is formed to allow fluid flow into the housing through the first opening.

15. The flow diversion device of claim 14, wherein, when the flow control component is in the first position, the first fluid pathway allows fluid to flow into the housing through the third opening and out of the housing through the first opening such that the first fluid pathway fluidly connects the third opening with the first opening.

16. The flow diversion device of claim 15, wherein, when the flow control component is in the first position, the second fluid pathway allows fluid to flow out of the housing through the fourth opening and into the housing through the second opening such that the second fluid pathway fluidly connects the fourth opening with the second opening.

17. The flow diversion device of claim 16, wherein, when the flow control component is in the second position, the third fluid pathway allows fluid to flow into the housing through the third opening and out of the housing through the second opening such that the third fluid pathway fluidly connects the third opening with the second opening.

18. The flow diversion device of claim 17, wherein, when the flow control component is in the second position, the fourth fluid pathway allows fluid to flow out of the housing through the fourth opening and into the housing through the first opening such that the fourth fluid pathway fluidly connects the fourth opening with the first opening.

19. The flow diversion device of claim 18, wherein the third opening is fluidly coupled to a fluid supply reservoir such that in both the first position and the second position of the flow control component, fluid flows into the housing from the fluid supply reservoir through the third opening.

20. The flow diversion device of claim 19, wherein the fourth opening is fluidly coupled to a drainage reservoir such that in both the first position and the second position of the flow control component, fluid flows out of the housing through the fourth opening to the drainage reservoir.

* * * * *